United States Patent
Streepy, Jr.

(10) Patent No.: US 7,120,646 B2
(45) Date of Patent: Oct. 10, 2006

(54) METHOD AND SYSTEM FOR INTERFACING WITH A MULTI-LEVEL DATA STRUCTURE

(75) Inventor: Larry V. Streepy, Jr., Ridgway, CO (US)

(73) Assignee: Health Language, Inc., Aurora, CO (US)

( * ) Notice: Subject to any disclaimer, the term of this patent is extended or adjusted under 35 U.S.C. 154(b) by 452 days.

(21) Appl. No.: 09/829,461

(22) Filed: Apr. 9, 2001

(65) Prior Publication Data

US 2002/0198885 A1    Dec. 26, 2002

(51) Int. Cl.
*G06F 7/00* (2006.01)
(52) U.S. Cl. .................. 707/104.1; 707/10; 705/2; 705/3; 715/713
(58) Field of Classification Search .......... 707/104.1, 707/3, 7, 10; 705/3, 2; 715/713
See application file for complete search history.

(56) References Cited

U.S. PATENT DOCUMENTS

| | | |
|---|---|---|
| 4,177,514 A | 12/1979 | Rupp |
| 4,839,853 A | 6/1989 | Deerwester et al. |
| 4,914,590 A | 4/1990 | Loatman et al. |
| 4,965,763 A | 10/1990 | Zamora |
| 4,974,191 A | 11/1990 | Amirghodsi et al. |
| 5,056,021 A | 10/1991 | Ausborn |
| 5,130,924 A | 7/1992 | Barker et al. |
| 5,325,293 A * | 6/1994 | Dorne ..................... 705/2 |
| 5,379,366 A | 1/1995 | Noyes |
| 5,386,556 A | 1/1995 | Hedin et al. |
| 5,594,837 A | 1/1997 | Noyes |
| 5,615,362 A | 3/1997 | Jensen et al. |
| 5,619,709 A | 4/1997 | Caid et al. |
| 5,630,125 A | 5/1997 | Zellweger |
| 5,644,686 A | 7/1997 | Hekmatpour |
| 5,696,885 A | 12/1997 | Hekmatpour |
| 5,706,506 A | 1/1998 | Jensen et al. |
| 5,720,007 A | 2/1998 | Hekmatpour |
| 5,742,811 A | 4/1998 | Agrawal et al. |
| 5,768,578 A | 6/1998 | Kirk et al. |
| 5,781,879 A | 7/1998 | Arnold et al. |
| 5,802,508 A | 9/1998 | Morgenstern |
| 5,806,056 A | 9/1998 | Hekmatpour |

(Continued)

OTHER PUBLICATIONS

Cerveri et al., Java Interface to Human Anatomy Knowledge, Euromicro Conference, 2000. Proceedings of the 26th, pp. 384-390.*

(Continued)

*Primary Examiner*—Shahid Alam
*Assistant Examiner*—Hung Pham
(74) *Attorney, Agent, or Firm*—King & Spalding LLP

(57) ABSTRACT

The present invention provides a method and system for interfacing with a multi-level data structure by selecting a concept object stored in the multi-level data structure, displaying a first image representing the selected concept object, displaying one or more second images generally above the first image, and displaying a first connector connecting each second image to the first image. Whenever the selected concept object has one or more child concept objects, one or more third images are displayed generally below the first image, and a second connector is displayed connecting each third image to the first image. Whenever the selected concept object has one or more lateral concept objects, one or more fourth images are displayed generally on one or both sides of the first image, and a third connector is displayed connecting each fourth image to the first image.

7 Claims, 20 Drawing Sheets

U.S. PATENT DOCUMENTS

| | | |
|---|---|---|
| 5,809,499 A | 9/1998 | Wong et al. |
| 5,819,270 A | 10/1998 | Malone et al. |
| 5,873,056 A | 2/1999 | Liddy et al. |
| 5,983,170 A | 11/1999 | Goodman |
| 6,083,276 A | 7/2000 | Davidson et al. |
| 6,178,416 B1 | 1/2001 | Thompson et al. |
| 6,219,632 B1 | 4/2001 | Schumacher et al. |
| 6,237,006 B1 * | 5/2001 | Weinberg et al. ....... 707/103 R |
| 6,243,669 B1 | 6/2001 | Heriguchi et al. |
| 6,260,008 B1 | 7/2001 | Sanfilippo |
| 6,275,789 B1 | 8/2001 | Moser et al. |
| 6,278,968 B1 | 8/2001 | Franz et al. |
| 6,282,507 B1 | 8/2001 | Horiguchi et al. |
| 6,282,538 B1 | 8/2001 | Woods |
| 6,304,259 B1 | 10/2001 | DeStefano |
| 6,314,566 B1 | 11/2001 | DeBusk et al. |
| 6,345,387 B1 | 2/2002 | Morrison |
| 6,353,817 B1 | 3/2002 | Jacobs et al. |
| 6,356,864 B1 | 3/2002 | Foltz et al. |
| 6,490,581 B1 * | 12/2002 | Neshatfar et al. ............... 707/4 |
| 6,618,733 B1 * | 9/2003 | White et al. ............ 707/103 Y |
| 2002/0010582 A1 | 1/2002 | Firman |
| 2002/0049600 A1 | 4/2002 | L'Esperance et al. |
| 2002/0198885 A1 | 12/2002 | Streepy |

OTHER PUBLICATIONS

UMLS Knowledge Sources, 8th edition, Jan. 1997, <http://www.medinfo.rochester.edu/umls/doc>.*

* cited by examiner

Concept Type Displayability Settings

| Concept Type | Plex | Attribute Table | Search Dialog |
|---|---|---|---|
| CPT | ☑ | ☑ | ☑ |
| First DataBank | ☑ | ☑ | ☑ |
| FOUNDATION | ☑ | ☑ | ☑ |
| HCPC8 | ☑ | ☑ | ☑ |
| ICD-10 | ☑ | ☑ | ☑ |
| ICD-10-AM | ☑ | ☑ | ☑ |
| ICD-9-CM | ☑ | ☑ | ☑ |
| ICPC | ☑ | ☑ | ☑ |
| MeSH | ☑ | ☑ | ☑ |
| NIC | ☑ | ☑ | ☑ |

872 — Concept Type; 874 — Plex; 876 — Attribute Table; 878 — Search Dialog

Check concept types that should be displayed for the respective components

*Fig. 8B*

Concept Type Displayability Settings

| | |
|---|---|
| GUID | |
| Concept Type Name | RoseBilling |
| Concept Type Nickname | RoseBilling |
| Description | Hierarchical Rose Billing Code |

836 — GUID; 838 — Concept Type Name; 840 — Concept Type Nickname; 842 — Description

*Fig. 8C*

Manage Facet Definitions — 1060, 1068

| Facet Name | Applicability |
|---|---|
| Billing Code | ☐T ☑C ☐M ☐E ☐R |
| CPT CODE | ☐T ☑C ☐M ☐E ☐R |
| HCPCS CODE | ☐T ☑C ☐M ☐E ☐R |
| ICD 10 AM BLOCK CODE | ☐T ☑C ☐M ☐E ☐R |
| ICD 10 AM CODE | ☐T ☑C ☐M ☐E ☐R |
| ICD 10 AM PROC CODE | ☐T ☑C ☐M ☐E ☐R |
| ICD 10 CODE | ☐T ☑C ☐M ☐E ☐R |
| ICD 9 CM CODE | ☐T ☑C ☐M ☐E ☐R |
| ICD 9 PROC CODE | ☐T ☑C ☐M ☐E ☐R |
| ICD-O Topography Code | ☐T ☑C ☐M ☐E ☐R |
| IUBMB Code | ☐T ☑C ☐M ☐E ☐R |
| MESH CODE | ☐T ☑C ☐M ☐E ☐R |

Edit — 1062
New — 1064
Delete — 1066

Microglossary Export Options Manager

Please specify the details of the export format

- 1253a — ○ Export as XML
- 1253b — ○ Export as Query Set
- 1253c — ● Export as CSV ☐ Exclude column headers — 1255

Facets to export:
- ICD 9 CM CODE
- ICD 9 PROC CODE
- ICD-O Topography Code
- IUBMB Code
- MESH CODE
- MG Facet
- SNOMED CODE
- SNOMED ID

— 1259

- 1257a — Field Quote String [ ]
- 1257b — Field Separator String [ ]
- 1257c — Value Quote String [ ]
- 1257d — Value Separator String [ ]

1261 — ☐ Sorted  ● By Term Text
              ○ By Facet Value  [Billing Code ▼] — 1265

[Back] [Next] [Cancel]

METHOD AND SYSTEM FOR INTERFACING WITH A MULTI-LEVEL DATA STRUCTURE

FIELD OF THE INVENTION

The present invention relates generally to the field of computer systems and, in particular, to a method and system for interfacing with a multi-level data structure.

BACKGROUND OF THE INVENTION

As demonstrated by the Unified Medical Language System ("UMLS"), merging multiple incompatible terminology "ideas" into one imposes a unity upon concepts that are not equivalent. This unification results in ambiguity of interpretation and a loss of structural integrity of the original coding system. While the UMLS has achieved the goal of imposing order upon unrelated data sets, it results in inappropriate representation of all the coding systems involved and, worse, true errors in the stated congruence of conceptual models.

Accordingly, there is a need for a multi-level data structure that provides a wide breadth of standardized knowledge, representing the concepts of every aspect of an enterprise. In addition, there is a need for a method and system that interfaces with the multi-level data structure and that enables easy access, use and maintenance of standardized knowledge relating to an enterprise.

SUMMARY OF THE INVENTION

The present invention provides a method and system for interfacing with a multi-level data structure that encompasses a wide breadth of standardized knowledge representing the concepts of every aspect of an enterprise. The multi-level data structure of the present invention provides concepts and relationships that provide controlled terminology completely capturing the language of an enterprise. Moreover, the multi-level data structure or knowledge model of the present invention provides for the accurate and complete representation of all terminology systems thereby maintaining the truth and integrity of each of those terminology systems.

In one representative embodiment of the present invention, an interface provides access to a multi-level data structure that has concepts and relationships that provide controlled medical terminology that completely captures the language of healthcare. The present invention also includes a multidimensional semantic content network. The interface of the present invention provides a language-modeling environment enabling the user to maintain and enhance the semantic content. A graphical user interface ("GUI") is also provided with which a user can easily navigate in order to use and maintain the terminology content.

The present invention provides a method for interfacing with a multi-level data structure by selecting a concept object stored in the multi-level data structure, displaying a first image representing the selected concept object, displaying one or more second images generally above the first image, and displaying a first connector connecting each second image to the first image. Each second image represents a parent concept object of the selected concept object. Whenever the selected concept object has one or more child concept objects, one or more third images are displayed generally below the first image, and a second connector is displayed connecting each third image to the first image. Each third image represents a child concept object of the selected concept object. Whenever the selected concept object has one or more lateral concept objects, one or more fourth images are displayed generally on one or both sides of the first image, and a third connector is displayed connecting each fourth image to the first image. Each fourth image represents a lateral concept object of the selected concept object.

The present invention also provides a computer program embodied on a computer readable medium for interfacing with a multi-level data structure. The computer program includes code segments for selecting a concept object stored in the multi-level data structure, displaying a first image representing the selected concept object, displaying one or more second images generally above the first image, and displaying a first connector connecting each second image to the first image. Each second image represents a parent concept object of the selected concept object. Whenever the selected concept object has one or more child concept objects, one or more third images are displayed generally below the first image, and a second connector is displayed connecting each third image to the first image. Each third image represents a child concept object of the selected concept object. Whenever the selected concept object has one or more lateral concept objects, one or more fourth images are displayed generally on one or both sides of the first image, and a third connector is displayed connecting each fourth image to the first image. Each fourth image represents a lateral concept object of the selected concept object.

In addition, the present invention provides a system for interfacing with a multi-level data structure that includes a computer, a display communicably connected to the computer, a memory communicably connected to the computer for storing the multi-level data structure, and a computer program resident on the computer. The computer program selects a concept object stored in the multi-level data structure, displays a first image representing the selected concept object, displays one or more second images generally above the first image, and displays a first connector connecting each second image to the first image. Each second image represents a parent concept object of the selected concept object. Whenever the selected concept object has one or more child concept objects, one or more third images are displayed generally below the first image, and a second connector is displayed connecting each third image to the first image. Each third image represents a child concept object of the selected concept object. Whenever the selected concept object has one or more lateral concept objects, one or more fourth images are displayed generally on one or both sides of the first image, and a third connector is displayed connecting each fourth image to the first image. Each fourth image represents a lateral concept object of the selected concept object.

BRIEF DESCRIPTION OF THE DRAWINGS

The above and further advantages of the present invention may be understood by referring to the following description in conjunction with the accompanying drawings in which corresponding numerals in the different figures refer to the corresponding parts in which:

FIG. 8B depicts an illustration of a LExScape graphical user interface display representing displayability settings in accordance with the present invention;

FIG. 8C depicts an illustration of a LExScape graphical user interface display representing a definition editor in accordance with the present invention;

FIG. 10B depicts an illustration of a LExScape graphical user interface display representing a definition management dialog box in accordance with the present invention;

FIG. 12E depicts an illustration of a LExScape graphical user interface display representing export formats in accordance with the present invention;

FIG. 16 depicts an illustration of a LExIndex graphical user interface display in accordance with the present invention.

DETAILED DESCRIPTION OF THE INVENTION

While the making and using of various embodiments of the present invention are discussed herein in terms of a controlled medical vocabulary engine, it should be appreciated that the present invention provides many applicable inventive concepts that can be embodied in a wide variety of specific contexts. The specific embodiments discussed herein are merely illustrative of specific ways to make and use the invention and are not meant to limit its scope in any way.

The present invention provides a method and system for interfacing with a multi-level data structure that encompasses a wide breadth of standardized knowledge representing the concepts of every aspect of an enterprise. The multi-level data structure of the present invention provides concepts and relationships that provide controlled terminology completely capturing the language of an enterprise. Moreover, the multi-level data structure or knowledge model of the present invention provides for the accurate and complete representation of all terminology systems thereby maintaining the truth and integrity of each of those terminology systems.

In one representative embodiment of the present invention, an interface provides access to a multi-level data structure that has concepts and relationships that provide controlled medical terminology that completely captures the language of healthcare. The present invention also includes a multidimensional semantic content network. The interface of the present invention provides a language-modeling environment enabling the user to maintain and enhance the semantic content. A graphical user interface ("GUI") is also provided with which a user can easily navigate in order to use and maintain the terminology content.

The controlled vocabulary engine and GUI of the present invention are centered around the Systematized Nomenclature of Medicine Reference Terminology ("SNOMED RT") of the College of American Pathologists. Added to this core are concepts and relationships that completely capture the language of healthcare. Additional terminology sets can be added to supplement the clinical foundation supplied by SNOMED RT. These terminology sets may include administrative terminologies, such as ICD and CPT, pharmacy terminologies, MeSH, UMLS CUI codes, and others that are necessary for the management of clinical healthcare.

Figure 1:
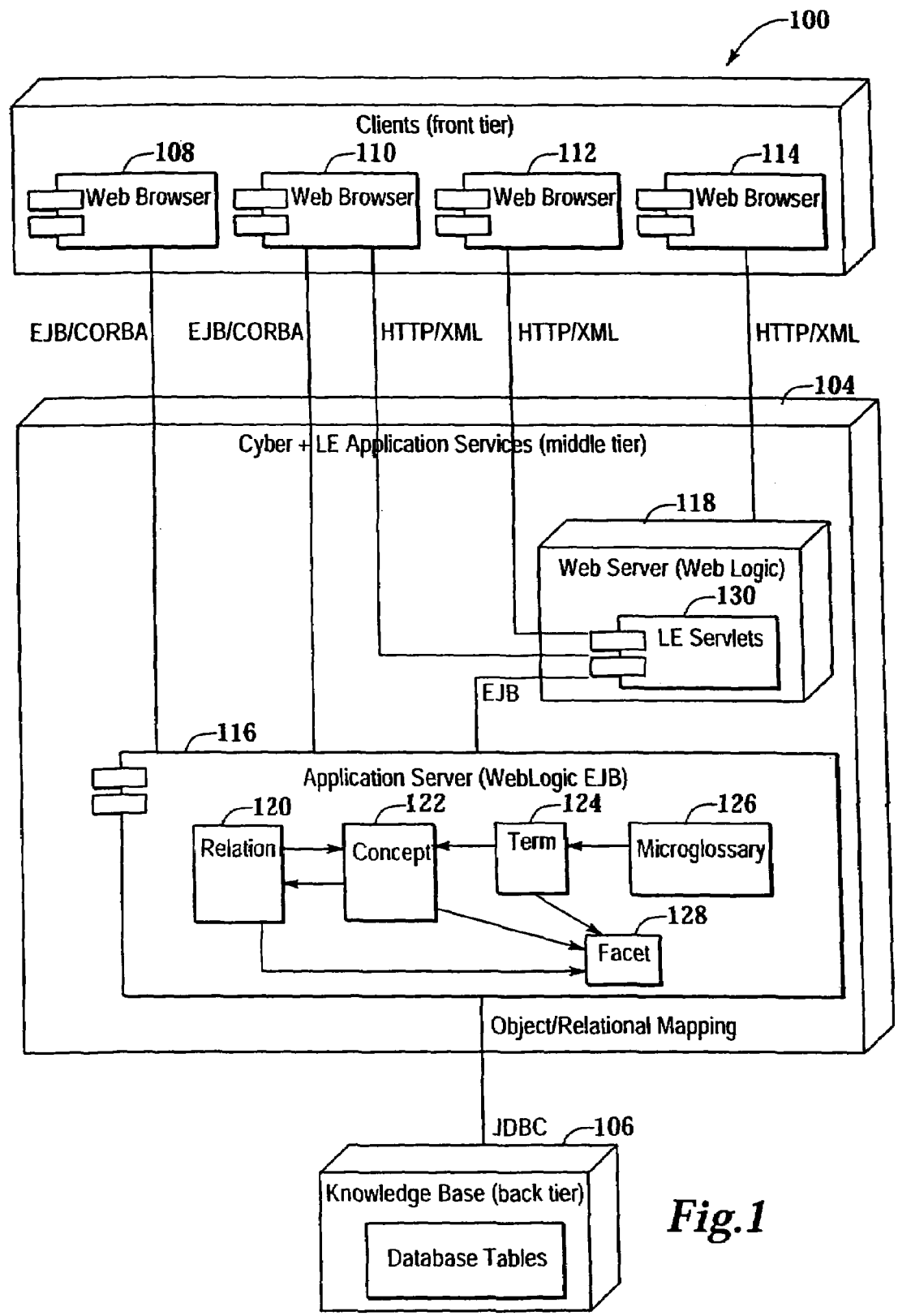
FIG. 1 depicts a deployment model of a language engine in accordance with the present invention.

Referring to FIG. 1, a deployment model of a language engine 100 in accordance with the present invention is shown. The language engine 100 uses a three-tier deployment architecture, which includes a front tier 102 for client applications, a middle tier 104 for application services and a back tier 106 for a knowledge base. This deployment model offers the benefit of proven services, such as scalability, fault tolerance, etc., while providing an application programmer with several alternatives to choose from, when it comes to integrating the language model and its content within their application. The multi-level data structure or language model and its content will hereinafter be referred to as "the Lexicon."

The Lexicon content provided by the present invention is unique in the industry in its breadth of coverage for Healthcare industry standards. In addition to providing SNOMED/RT as the clinical foundation, the Lexicon contains the administrative terminologies needed in today's healthcare environment: The diagnosis and procedure codes (e.g. ICD 9 CM, ICD10, ICD 10AM) needed by billing applications; drug codes needed by pharmacy applications (e.g., FDB and Multum), MeSH codes needed by literature search engines and more. While SNOMED RT provides a clinical foundation, administrative terminologies are logically mapped to their SNOMED RT counterparts and to each other, as appropriate.

The main service mechanism is delivered using a three-tier deployment architecture with access provided through Enterprise JavaBeans ("EJB") and Common Object Request Broker Architecture ("CORBA"). The present invention facilitates local, enterprise-specific modifications and additions to the terminology content. New concepts can be added and linked to the reference standards. Unique concepts, such as charges, can be added. Microglossaries (term lists) can be managed for specific applications.

Figure 2:
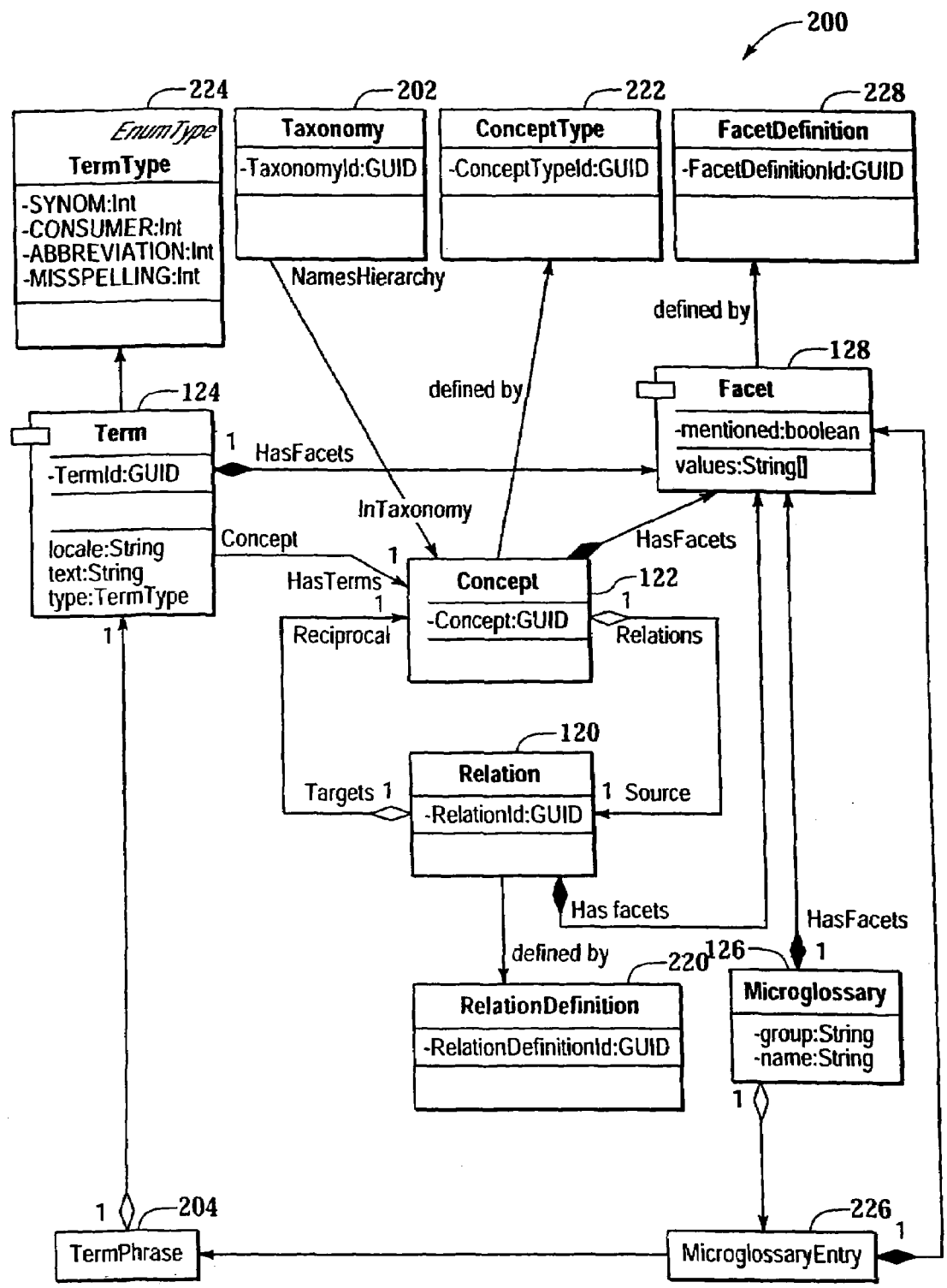
FIG. 2 depicts an object model of a language engine in accordance with the present invention.

The front tier 102 client applications include various applications that provide access to the middle tier 104 application services and thus control of the language model and its content. The front tier 102 client applications may include LExScape 108, Vendor applications 110, LExIndex 112 and Web Browser 114. LExScape 108 is a graphical user interface ("GUI") for browsing and manipulating the Lexicon. A screen shot of LExScape 108 is depicted in FIG. 2. LExScape 108 is a content management facility for use by administrators and content editors of the Lexicon. Vendor applications 110 are user specific applications that access the middle tier 104 application services. LExIndex 112 is a GUI for indexing (or tagging) documents with concept identifiers. Web Browser applications 114 allow users to access the middle tier 104 application services via a wide area network, such as the Internet.

The middle tier 104 application services include an Application Server 116 and a Web Server 118. The Application Server 116, such as BEA's WebLogic, provides the Enterprise Java Bean ("EJB") server and container that provide access to the exposed object model via standard remote and serialized objects. The object model includes core objects, such as Relation 120, Concept 122, Term 124, Microglossary 126 and Facet 128, that will be discussed in more detail in reference to FIG. 2. The core objects 120, 122, 124, 126 and 128 are implemented as visible EJB objects (i.e., accessible remotely), while supporting objects are passed as serialized objects. This model properly optimizes and makes trade-offs between round-trip method invocation time and EJB modeling. The EJB objects are also made available as CORBA objects (using IIOP). This provides support for distributed access from non-Java environments. The Application Server 116 may be hosted on either a Windows NT, Windows 2000, or AIX platform.

The Web Server 118 hosts servlets 130 that provides access to the Lexicon via an HTML/XML data stream over HTTP. The Web Server 118 provides servlet-based functionality, such as indexing and searching, when the full power of LExScape 108 is not needed. For example, LExIndex 112 uses the servlet 130 to perform the indexing operation and retrieve the index results. When accessed by LExIndex 112 using an HTTP GET operation, the servlet 130 returns a simple web form that can be used to access the indexing services. When a URL or text buffer is submitted, an HTTP POST operation is sent back to the same servlet 130. In response to the POST operation, LExIndex 112 retrieves the contents of the indicated URL (or text buffer) and then indexes the document using the requested query set. The results of the index operation are returned to the client in an XML document.

The database tier 106 handles the relational database that holds the Lexicon, mapped into relational form. The middle tier 104 provides the necessary relational-to-object mapping for the database. Access to the database is made through JDBC from within the Application Server 116. Preferably, application programmers are not provided direct access to the back tier 106. The Lexicon utilizes a highly optimized, simple dB schema to hold the relational form of the Lexicon. The present invention supports the use of MS SQL Server 7.0 and Oracle 8i running on a Windows NT or Windows 2000 Server platform, and Oracle 8i running on AIX.

The present invention provides an application programming interface ("API") having three major functional categories: (1) Direct and Related Object Access; (2) Searching; and (3) Exporting. Each of the objects in the model has a unique identifier. This identifier can be used to directly access the object on the server. For example, an application may store the Concept ID during data entry and then later access that Concept 122 via the stored ID. Each object API provides methods for accessing the related objects. For example, from a Concept 122, you can obtain all the associated Terms 124. From a Term 124, you can access the associated Concept 122. Navigation between objects is simple and intuitive.

The API includes a wide variety of search capabilities. Client applications can search for Concepts 122 by any of the following attributes: (1) by a specified Term type's text (the text of a Synonym, for example); by the text of any related Term 124 or by the value of a specified Facet 128, such as SNOMED code. On any of these searches, wildcards may be used. For example, one could search for Concepts 122 that have an ICD-9 code starting with "207." Further, the search may be constrained to locating Concepts 122 in a specified Taxonomy 202 (FIG. 2), or of a given Concept-Type 222 (FIG. 2). Client applications may search for Terms 124 by any of the following attributes: (1) by text; or (2) by text and a specified Term type (only misspellings, for example). In addition to the above search mechanisms, client applications can also search Microglossaries 126 for term text or facet values.

The present invention can be used to provide data to applications that will not be continually connected to the Lexicon server by exporting data to external files. Exports can be made of specified Concepts 122, entire sub-hierarchies, and Microglossaries 126. The client has control over exactly what data are exported and the format of the export, such as XML, Comma-separated Values (CSV), or Query Set (intended for use in generating query sets to be used by the LExIndex tools).

The system can be accessed by logging-on through the use of a user ID and password. Security permissions are assigned on an individual or group basis, through the user ID. Security permissions determine the types of modeling activities that a user can perform. Some users may be limited to merely viewing, while others may be given full access to the entire range of functions available in the system. A "content administrator" has the highest access. Only content administrators may make changes that can potentially alter SNOMED RT or other coding systems.

Now referring to FIG. 2, an object model 200 of a language engine in accordance with the present invention is shown. Object model 200 includes the following objects: Concept 122, Relation 120, Facet 128, ConceptType 222, RelationDefinition 220, FacetDefinition 228, Taxonomy 202, Microglossary 126, MicroglossaryEntry 226, Term 124, TermType 224 and TermPhrase 204. The Lexicon is exposed to client applications 108, 110, 112 and 114 (FIG. 1) via object model 200. Objects that need to be remotely accessible are implemented as EJB objects, while those that are not are implemented as serialized objects. FIG. 2 uses UML syntax to represent the Lexicon objects and their associations. Information regarding UML syntax can be found at the web site http://www.rational.com/uml/index.jt-mpl.

The present invention provides an "aligned model" for representing terminology standards. This means that each standard is uniquely represented and then alignments (relationships) are created between the concepts in each standard. The power of this object model 200 lies in the understanding that the relationships between terminology systems must be represented independently of the conceptual ideas within the individual terminologies. This approach to terminology modeling provides unparalleled ability to represent and access the multitude of terminology standards in a specified field while remaining open to extension and enhancement by the end-user.

The object model 200 is preferably a meta-model, which means that the customer can define entirely new model component types. The use of a meta-model enables the present invention to accurately and completely represent nearly any terminology standard. Instead of trying to force each standard into a rigid, pre-defined structure, the object model 200 can be adapted to represent the standard in its true form.

The meta-model components define the attributes, or properties, for instances of each model type. For example, ConceptType 222 defines instances of Concept objects 122, RelationDefinition 220 defines instances of a Relation 120, and FacetDefinition 228 defines instances of a Facet 128. This defining relationship is comparable to the relationship between a Class definition and a Class instance in object oriented programming languages.

Each of the major terminology systems, such as SNOMED RT, ICD-9 and MeSH, are defined as unique Concept types 222. This allows the present invention system to recognize that the "ideas" represented in the terminology are defined within different logical realms. Even though Concepts 122 from different types can be related, they are not the exact same idea. For example, the concept of "Diabetes Mellitus" in SNOMED RT is related to the concept of "Diabetes Mellitus" in ICD-9, but they are fundamentally different ideas.

A RelationDefinition 220 essentially defines a unique way in which one or more Concepts 122 may be related. The present invention comes pre-configured with several useful RelationDefinitions 220. For example, the IS-A RelationDefinition 220 defines a hierarchical relationship between two Concepts 122 where one concept is the "parent" and one is the "child". Further, the parent is more general than the child and the child is more specific than the parent. Another example is "SNOMED-ICD_9", a relation that provides a correspondence between a SNOMED concept and it's closest (semantically similar) concept within ICD-9.

As mentioned above, Facets 128 are the mechanism used to store attributional data on an object within the Lexicon content. All of the core model components can have attributes, including Concept 122, Term 124, Relation 120, Microglossary 126, and MicroglosaryEntry 226 objects. The FacetDefinition 228 specifies the properties of a type of Facet 128, including the restrictions on which types of object Facet 128 instances may be applied (e.g., a modeler may wish to restrict the use of a Facet 128 to only Term objects 124), and constraints on the values the Facet 128 instances may hold (such as restricting values to integers or floating point numbers).

All of the meta-model components share a set of common properties: (1) a Globally Unique ID ("GUID"); (2) a localized display name; (3) a localized description; and (4) a nickname. The GUID is a unique ID of the object that is a large string of meaningless numbers used to uniquely identify all the major objects in the system. Preferably, the algorithm used to generate a GUID ensures the no two systems can generate the same GUID. The localized display name is specific to a given language locale, such as "en_US" for US English. Each component can have multiple display names associated with it so that multiple languages can be supported. Likewise, the localized description allows multiple descriptions to be associated with each meta-model component. The Nickname eases access from within customer written applications, meta-model components each have a text nickname. This nickname must be unique among all the objects of a given type. Finder methods allow an application to locate a component by nickname. Thus, an application can locate the ConceptType 222 for SNOMED RT by doing a lookup on the nickname "SNOMED_RT" instead of embedding the GUID (a string of 32 hex digits) constant within their application. This increases readability and maintainability of the customer written code.

Each major terminology system (such as SNOMED, ICD-9, or MeSH) is defined as a unique ConceptType 222. This allows the present invention to recognize that the "ideas" represented in the terminology are defined within different logical realms. Even though Concepts 122 from different types can be related, they are not the exact same idea. For example, the concept of "Diabetes Mellitus" in SNOMED is related to the Concept 122 of "Diabetes Mellitus" in ICD-9, but they are fundamentally different ideas.

The use of ConceptTypes 222 is not limited to representing medical terminologies. For example, assume that an enterprise wants to store within the lexicon supplies that can be consumed during various procedures. They can create a new ConceptType 222 to contain the supply objects and then relate each procedure to the supplies that are, or can be, used during that procedure. There is no limit to the types of data that can be modeled and correlated within the lexicon.

A RelationDefinition 220 essentially defines a unique way in which one or more Concepts 122 may be related. Each Relation 120 has a single "source" Concept 122 and the instance relates that source to one or more "target" Concepts 122. Since most terminology standards utilize a hierarchical, or taxonomic structure, the present invention comes with a parent/child relation already defined. The parent/child relation (also called an IS-A relation) defines a hierarchical relationship between two Concepts 122 where one concept is the "parent" and one is the "child", the parent being a more general idea than the child. The parent/child relation also defines a classification system wherein the child is classified as a "kind of" the parent. For example, the Concept 122 of "Peptic Ulcer" is a child of "GI Ulcer" which is a child of "Disease of GI tract" which is (skipping some intermediate concepts) a child of "Disease. Thus, "Peptic Ulcer" is a more specific form of "GI Ulcer" and it is classified as a "Disease". Further, the Concept 122 of "Peptic Ulcer" has a relationship (of type "Associated Topography", as defined by SNOMED) to the "Upper GI tract", meaning that this disease affects the upper GI tract.

SNOMED RT, for example, defines numerous "role" relationships. These roles provide additional semantic definition to the medical concepts that are being related. The present invention represents each of these role types using a RelationDefinition 220. Then, instances of the Relation 120 embody the specific relationships defined by SNOMED RT. A few of the roles are explained below for clarity.

Associated Topography For disorders, names the site affected by a condition, or the affected site resulting in a condition. For procedures, names the anatomical site affected by a procedure.

Associated Function Relates a finding or disorder to its associated biologic function. Whereas lung cancer has topography of "Lung", a voice disorder has functional feature "voice". There is no topographical location for voice since it really has no one single site that creates it. A sexual disorder would have functional feature "sex" or "sexual behavior."

Branch Of Names the relationship of arteries, veins, nerves, lymphatics, and other similar structures to their branches.

Procedure Approach Names the directional, spatial, or relational access to the topographic site of a procedure. An "excision of the leg by cutaneous approach" has a procedural approach of "cutaneous approach"

Relations 120 allow one to richly articulate the complex interactions of medical information. In its simplest form a "relation" allows us to say that the clinical disease, "Diabetes Mellitus" is equivalent to the billing code ICD-9 "250". Equivalent relations are often referred to as "crosswalks" or "crossmaps" and the present invention comes with a rich assortment of these crosswalks. Even simple relations such as these can be made more complex in the medical realm when one considers the reciprocity of relations. If we assert that "A" is related to "B", it may also be true that "B" has some relation to "A". The knowledge model supports the definition of such reciprocal relations, with the full understanding that they are not always true and must be carefully articulated. Further, relations between billing codes and clinical notions may not be one-to-one. That is to say that a given ICD-9 code may be more specific than, equal to, or more general than its related clinical Concept 122. The knowledge model allows such clarifications to be expressed with the "Relationship" property, see below for details.

But Relations 120 are useful for more than just saying that two things are equivalent. They provide a robust mechanism for specifying arbitrary types of relationship between objects. It is these complex relations that allow us to represent the information needed by medical logic modules, billing modules, rules engines, and more.

For example, a medical logic module might depend upon relations in the lexicon to support the following alerts: (1) alert the clinician to do an eye exam whenever the diagnosis of diabetes is made; and (2) if the diagnosis of meningitis is made, make sure the patient has neck stiffness and fever. In another example, a billing logic module might depend upon relations in the Lexicon to send an ICD-9 code ("250") to a billing application each time a clinician enters a diagnosis of "Diabetes Mellitus." In yet another example, a business logic module might depend upon relations in the lexicon to assert enterprise policy: (1) if an upper GI series is ordered, a GI consult is required; and (2) if a 5$^{th}$ generation antibiotic is ordered, an Infectious Disease consult is required.

Each RelationDefinition 220 holds the properties that define characteristics of the instances of the relation type. The salient properties are listed below.

| Property | Description |
| --- | --- |
| Displayable | Whether instances of this relation should be displayed (by default) within visual clients. |
| Immutable | Indicates if, once an instance of this relation is created, it can be modified or removed by the standard modeler security level. This setting provides support for controlling the modifiability of relations defined by external standards (like SNOMED) or by vendor customers that wish to prevent their customers from modifying pre-defined relation instances. |
| Hierarchical | Indicates if this relation is hierarchical in nature. Hierarchical relations can be used by LExScape to provide a hierarchy view. By definition, the source Concept 122 is "greater than" the target Concept 122 in the hierarchy; i.e., the source is the parent and the target is the child. |
| Inheritance | Indicates if facet values inherit along this relation |
| Inheritable | Indicates if this relation is inheritable along hierarchical lines. If true, then when a parent is added to a concept 122 (or a new child is created), then the parent's values for this relation will be inherited by the child 122. |
| Cardinality | Either single (1:1) or multiple (1:M). |
| Ordered | For 1:M relations, indicates if the set contents are ordered. |
| TypeRestriction | Indicates the restrictions, if any, on the source and target concept types. Possible values are: <br> None — No restrictions <br> Equal — The types are not individually restricted, but the source and target must be of the same type. <br> LimitSource — Limits the source concept type to the type indicated in the SourceType property. <br> LimitTarget — Limits the target concept type to the type indicated in the TargetType property. <br> LimitBoth — Limits the source and target concept type to the types indicated in the appropriate property. |
| SourceType | If used, this is a ConceptType ID indicating that this relation can only be applied to Concepts of that type. |
| TargetType | If used, this is a ConceptType ID indicating that this relation can only be targeted at Concepts of that type. |
| Relationship | In essence, how do the concepts 122 compare to each other. The options are: <br> None — The concepts are simply related, no comparison is being made. <br> Equal — They are equivalent concepts. <br> More general — The source Concept 122 is more general than the target Concept 122. <br> More specific — The source Concept 122 is more specific than the target Concept 122. <br> Note that "More general" and "More specific" are commonly used to relate coding concepts to foundation (clinical) concepts. |
| Transitive | Indicates if this is a transitive relationship. That is, if Concept A is related to Concept B, which is related to Concept C, is Concept A related to Concept C? |
| Acyclic | If this Relation 120 is hierarchical, then this property is always TRUE. For non-hierarchical Relations, this flag indicates whether the server must enforce acyclic relationship graphs. |
| Reciprocal | A flag indicating if this Relation 120 can be viewed in a reciprocal (inverse) manner. For example, the inverse of "Has Parts" is "Part Of". Some relations may not reasonably be, or make no sense when inverted. |
| ReciprocalName | If Reciprocal is TRUE, then this field provides the display name to use when referencing the reciprocal view of a relation. |

A FacetDefinition 228 defines the properties of facet values that can be applied to many of the core model objects. Facets 128 can be applied to Concepts 122, Relations 120, Terms 124, Microglossaries 126, and MicroglossaryEntries 226. Facets 128 are attributional data, often application-specific, associated with a model object.

Facet values are used to represent the "code" values that most terminology standards associate with a conceptual object within the terminology. For example, the SNOMED Code associated with a specific concept is stored in a facet value on that Concept 122 object, and the SNOMED Description Id associated with a term is stored in a facet value on the Term 124 object. Similarly, the ICD-9 code is associated with an ICD-9 concept using a facet value.

Facets 128 are the typical place that an application would store information regarding a model object, such as a cost code, or ancillary ordering code for a Concept 122 that represents an orderable test. Another example, applicable to an e-commerce setting, would be to store identifiers indicating items for sale that are related to a specific symptom or diagnosis, such as syringes or blood test kits for Diabetes.

Each FacetDefinition 228 holds the properties that define characteristics of the instances of that Facet type. The salient properties are listed below.

| Property | Description |
| --- | --- |
| Displayable | Whether instances of this Facet 128 should be displayed (by default) within visual clients. |
| Value Type | Controls the type of values that can be specified in instances of this Facet 128. Options are:<br>String  Any value.<br>Integer  Values must be strings that are legal integer numbers, e.g., 12345.<br>Float  Values must be strings that are legal floating-point numbers, e.g., 54.321. |
| Immutable | Indicates if, once an instance of this Facet 128 is created, it can be modified or removed by the standard modeler security level. This setting provides support for controlling the modifiability of facet values defined by external standards (like SNOMED) or by vendor customers that wish to prevent their customers from modifying pre-defined facet instances. |
| Inheritable | Indicates if this Facet 128 is inheritable along hierarchical lines. If true, then when a parent is added to a Concept 122 (or a new child is created), then the parent's values for this Facet 128 will be inherited by the child. |
| Cardinality | Either single or multiple. Single cardinality facets can only have a single value, while multiple cardinality facets may have multiple values. Cardinality has a specific impact on inheritable facets, as shown in the table below. |

Note that the Inheritability and Cardinality attributes of a FacetDefinition 228 interact as defined in the table below.

|  | Non-Inherited | Inherited |
| --- | --- | --- |
| Single Cardinality | The Facet 128 may be given only a single value and it will apply only to the Concept 122 on which the Facet 128 is mentioned. None of that Concept's 122 descendents are affected. In essence this type of Facet 128 is local to the Concept 122 on which it is placed (mentioned). | The Facet 128 will apply to the Concept 122 on which it is mentioned and to all of that Concept's 122 descendents. If a Concept 122 inherits the Facet 128 from multiple parents, only a single value will be selected. Further, a Facet 128 of this type placed (mentioned) on a given Concept 122 overrides any value it might inherit from its parents, and this new value is then inherited down to all the descendents of said Concept 122. |
| Multiple Cardinality | The Facet 128 may be given one or more values and they will apply only to the Concept 122 on which the Facet 128 is mentioned. None of that Concept's 122 descendents are affected. In essence this type of Facet 128 is local to the Concept 122 on which it is placed (mentioned). | The Facet 128 may be given one or more values and they will apply to the Concept 122 on which it is mentioned and to all of that Concept's 122 descendents. If a Concept 122 inherits the Facet 128 from multiple parents, all the values from all the parents are accumulated. Any value for a Facet 128 of this type mentioned on a given Concept 122 is added to the set of values inherited to further descendents. |

The core, or central object within the Lexicon is the Concept 122. As described above, it represents a "unique entity of medical domain knowledge." Its defining Concept-Type 222 categorizes each Concept 122. Every Concept 122 has at least one parent Concept 122 and zero or more child Concepts 122 (determined by instances of the CHILD relation type). Concepts 122 that have no children are referred to as leaf Concepts 122.

A Concept 122 may represent something as broad as "Diagnosis" (i.e., the class of all diagnoses), to extremely granular entities necessary for clinical documentation, such as "Biliary Calculus (or Gallstone)." Concepts 122 are organized into a multi-axial hierarchy. This means that a Concept 122 can have multiple parents, i.e., it can reside in multiple classifications. For example, the Concept 122 representing "Bacterial Pneumonia" is classified within "Infection of Trunk" as well as within "Bacterial Infectious Disease." Each Concept 122 should be unique and distinct from all other concepts.

Much of a Concept's 122 meaning stems from its relations to other concepts. Its parentage determines the classification of the Concept 122, while the Concept 122 itself determines one level of classification for all its descendents. Its non-hierarchical relations can specify additional semantic context. For example, the SNOMED Roles associate a Concept 122 with affected topographic location, morphologies, etc. Concept 122 objects may have an arbitrary number of Facets 128. However, essentially all the interesting data regarding a Concept 122 resides in other objects associated with the Concept 122 object. These objects are discussed below.

Terms 124 hold the words used to verbalize a Concept 122. Terms 124 are organized within language locales (such as "en_US") to support international usage. Terms 124 are also the words used to document an encounter with a patient. When a physician documents that a patient has a broken leg, the phrase used to do so comes from the Term 124 associated with the Concept 122 of "Broken Leg". Each Concept 122 can have numerous Terms 124 associated with it, but each Term 124 object is associated with exactly one Concept 122 object. Each Term 124 has a number of attributes that further define its applicability for different uses. The attributes are: (1) the language locale in which this Term 124 is used, "en_US" for example; (2) the text string, as in "Broken Leg", (3) Display Term, which marks the Term 124 that should be used by default to display the associated Concept 122 (This term is the one LExScape uses to render the nodes in the Concept Display); and (4) the Term Type 224, which indicates the primary use of the Term 124. Term objects 124 may have an arbitrary number of Facets 128.

The various TermTypes 224 are listed below:

| | |
|---|---|
| Synonym | The set of Synonym terms for a Concept 122 are all the standard ways of expressing the Concept 122. The use of synonymous Terms 124 is the standard method for providing local variations in terminology, both for an Enterprise and for individual caregivers. |
| Consumer Term | A "common name" or colloquialism for a medical Concept 122. For example, the Term "Pass out" is a consumer Term for "Syncope". |
| Grammatical Variant | Grammatical variants, noun and verb tenses, etc., of the preferred Term 124 or synonym. For example, "nervousness" vs. "nervous", "break" vs. "broken". |
| Abbreviation | An accepted abbreviation or shortened form. For example, "Coronary Artery Bypass Graft" is often abbreviated as "CABG." |
| Misspelling | A common misspelling of another Term 124. Misspellings can be entered to aid in searching, especially when supporting lay people. Note that misspellings should never be used to document, but are useful information for locating Concepts. |
| Short | Many coding systems use lengthy, detailed text strings to refer to Concepts 122. These lengthy strings are often truncated for use by applications. The only difference between these terms is the length, or detail, of the phrase. This term type indicates a "short" phrase for the Concept 122. Note that the determination of what is short, medium, or long is up to the creators of the coding system. |
| Medium | A "medium" length phrase. |
| Long | A "long" phrase. |
| Coding Modifier | The term type "Coding Modifier" indicates a term that must be used in the context of the hierarchy in which it lives. An example from ICD-10 is a term "Lips". Out of the context of the hierarchy, it is not meaningful (worse it is ambiguous). However, within the context of the hierarchy, this term indicates a sub-classification of the parent concept ("Malignancy of") clarifying its usage to the "Lips". |

Each Concept 122 object may have an arbitrary number of Relation 120 instances associated with it. A Relation 120 is a connection between one or more Concepts 122. A relation 120 provides an explanation for the way in which two concepts interact with one another. IS-A (parent-child or hierarchical) relations suggest a relation in which the parent concept is larger/broader and the child concept is more granular. Each Relation 120 instance holds the Concept Id (GUID) of the source Concept 122 and the target Concept(s) 122. All the pertinent information regarding the usage of the Relation 120 is specified in the RelationDefinition 220. Each instance of a Relation 120 is either mentioned or inherited. When a Relation 120 is created on a given source Concept 122, the Relation 120 is mentioned on that Concept 122. If the RelationDefinition 220 indicates that the Relation 120 is inheritable, then inherited instances of the Relation 120 will be added to all the descendents of the original source Concept 122. Note that in each inherited Relation 120, the source Concept 122 is the current descendent, not the original source Concept 122. Inherited Relation 120 instances cannot be modified. Relation 120 objects may have an arbitrary number of Facets 128.

A role relation is a special type of relation strictly defined by SNOMED to suggest horizontal relations that are definitional and not assertional. Example: "Asthma" has topography "tracheobronchial tree" is a SNOMED role relation. It relates two distinct concepts (a diagnosis and a body part, in this example) in a defining way.

Arbitrary Relations can be used in many ways to associate concepts of interest. For example, a SNOMED clinical diagnosis can be related to its ICD billing code. This would permit an interaction between a clinical documentation system and a billing application. Or an agency might wish to link a clinical diagnosis with its common symptoms to fuel a decision support system.

A FacetDefinition 228 defines each Facet 128 instance. The core model objects can have Facets 128 that hold attributional information about the object. Facets 128 are the typical place that an application would store information regarding an object, such as a cost code, or ancillary ordering codes. Facets 128 are also used to hold the "code" values defined by most terminology standards. Facets 128 can be applied to the following object types: (1) Concept 122; (2) Term 124; (3) Relation 120; (4) Microglossary 126; and (5) MicroglossaryEntry 226.

When applied to Concept 122 objects, each instance of a Facet 128 is additionally defined as mentioned or inherited. When a Facet 128 is created on a given Concept 122, the Facet 128 is mentioned on that Concept 122. If the FacetDefinition 228 indicates that the Facet 128 is inheritable, then inherited instances of the Facet 128 will be added to all the descendents of the original Concept 122. Inherited Facet 128 instances cannot be modified, but they can be overridden by mentioning an instance of the Facet 128 on a descendent of the original Concept 122. The cardinality of the Facet 128 determines how inherited and mentioned Facets 128 interact.

Each Concept 122 is uniquely categorized by its defining ConceptType 222. Concepts 122 may be additionally categorized into Taxonomies 202. A Taxonomy 202 object is applied to a single Concept 122 object and defines a named sub-hierarchy of the Lexicon content. All the descendents of the target Concept 122 are part of the Taxonomy 202. The taxonomy name can then be used to constrain certain operations, such as searching, to Concepts 122 that reside within the sub-hierarchy. For example, the "Disease" taxonomy refers to the entire sub-hierarchy containing the Concept "Disease" and all of its descendants. Enterprises may specify their own names for identified sub-hierarchies and use them to bound searches or control exports.

As the name implies, a Microglossary 126 is a subset list (micro) of Terms 124 (glossary) from the Lexicon allowing users to view a custom subset of the Lexicon content rather than viewing the entirety of the Lexicon content. These Term 124 lists can be used for any purpose, at the discretion of the application designers. Typical uses are for creating "pick" lists for use within an application to speed structured data entry during an encounter. For example, a Microglossary 126 could be created that contains the top 25 chief complaints that a GP sees every day. Another example would be a list of medications that the Pharmacy has decided to carry for specific treatments, such as Beta-blockers. Microglossaries 126 are provided primarily for application use.

A Microglossary 126 contains an ordered list of MicroglossaryEntry 226 objects, described below, and an associated ExportContext. A Microglossary 126 can be exported to an external file. At the time of the export, the application (or user via LexScape 108) can select which attributes are to be exported. For example, an application may export the Term text, the related Concept ID, and the Concept's SNOMED ID. The ExportContext saves the settings from the last export performed on a Microglossary 126. This allows for an automated re-export using the same settings. Microglossary 126 objects may have an arbitrary number of Facets 128.

Facets 128 can be applied to entire Microglossaries 126 to provide application-level information about an entire list. For example, a Microglossary 126 containing blood tests required for management of pregnant patients may have a Facet 128 that contains an instruction to display this list only for Obstetric encounters. Similarly a Microglossary 126 containing drugs to treat asthma in children might have a Facet 128 to constrain display of the list to encounters with pediatric patients.

Each entry in a Microglossary 126 contains the following: (1) the TermPhrase 204, which is an object holding one or more Term 124 references; and (2) a set of Facets 128. Facet values placed on a MicroglossaryEntry 226 provide a mechanism to associate data with a Term 124 "in context" of the MicroglossaryEntry 226. Facet values associated with a MicroglossaryEntry 226 are intended to provide a simple storage area for use by the application developer. With proper application support, this allows individual caregivers to manage their own term lists.

As another example, a Pharmacy could provide a Microglossary 226 of drugs orderable for certain conditions, in this case Beta-blockers. Based upon negotiated contracts, supply, or other factors, the Pharmacy manager will determine the "Beta-blocker of choice" on a semi-regular basis. Instead of having to notify every prescribing physician, the Pharmacy manager could simply assign a DRUG_CHOICE of "BETA1" to the drug of choice. Now, the physician that wants to prescribe a Beta-blocker and doesn't need a specific drug (based on other findings) can simply order "BETA1". This provides the Pharmacy with the control they need to manage costs in a manner that is extremely simple to administer.

The use of Facet values on MicroglossaryEntry 226 objects provides for "in context" information, i.e., the facet value is unique to the combination of Microglossary 126 and Term 124. It is often inappropriate to place a Facet value on the Term 124 object, since there is no "context" for the Term 124 object. In the example above, it might not be appropriate to place the "BETA1" facet value on the Term "Atenolol", so the value is placed on the MicroglossaryEntry 226 in the specific formulary (Microglossary 126) in which it is located. In another formulary, possibly for use at a different clinic, Atenolol may not be the preferred beta-blocker, and in that MicroglossaryEntry 226 it would not have the "BETA1" facet value.

A TermPhrase 204 is an ordered set of one or more Terms 124 that represent a collection of Concepts 122, such as "Dialysis without complications". TermPhrase 204 objects live strictly within a given MicroglossaryEntry 226 object. They have no life beyond their use in a Microglossary 126. Each TermPhrase 204 holds either a single term, or multiple, ordered Terms 124. If the TermPhrase 204 holds multiple Terms 124, it is said to be compound. Compound TermPhrase 204 objects are primarily used for rapid documentation and to handle combinatorial coding sets required by applications. A new Concept 122 could be created to represent the combination of Terms 124, but that could lead to combinatoric explosion and general, non-useful clutter within the Lexicon. The TermPhrase 204 object should address existing incompatibilities between coding schemes of vastly different granularities that could not otherwise co-exist in the same data source.

Referring now to FIG. 3, an illustrative example of the LexScape 108 graphical user interface display in accordance with the present invention is shown. LexScape 108 provides a fully graphical, highly intuitive, interface with which users navigate the multidimensional semantic network of the Lexicon content. LExScape 108 provides the language-modeling environment used to maintain and enhance the Lexicon content. The display 300 includes several adjustable viewing areas. Concept display 305 is the viewing area of the graphical user interface ("GUI") where the lexicon is depicted graphically. The selected or focus concept 310 is the concept that is being worked on. Images representing the concepts or concept objects are typically displayed as text strings, which is usually the name of the displayed concept. Its facets and relations are listed in attribute panel 330. Lateral relation 315 depicts other concepts connected to the focus concept. A line or other type of connector between the two represents either a lateral relation or navigational line, such as navigation line 320. The appearance of a target concept and line connecting it with its source concept is an aid to navigation that remains only for the duration of the current work session. Pushpin 325 enables the user to stack multiple attributes panels 330 or term facet panels 355. The user can click pushpin 325 to retain a panel while navigating to other concepts. Clicking a panel tab brings that panel to the front. To remove a tacked panel, the user clicks that panel's tab to bring it to the front and then clicks pushpin 325 to release it.

Attribute panel 320 lists the lateral relations and facets of focus concept 310. Concept details 325 contain details relating to focus concept 310 such as its unique identifer, type, and taxonomy. Term panel 340 lists names for focus concept 310. Term panel 340 also indicates such information as the display name, a retired term, text and type for focus concept 310. Workbench 345 is the work area where the user can temporarily store terms and term phrases while modifying them. Microglossaries tab 350 displays the microglossaries panel. This panel will be blank until a microglossary has been created. Term facets tab 355 displays the term facets panel. Relation facets tab 360 displays the relation facets panel. Relation facets provide arbitrary data that may be stored in relations. Term phrase editor tab 365 displays the term phrase editor that is used to build phrases that can be stored as microglossary entries. Status bar 370 displays informational messages about system status and activities.

Figure 3A:
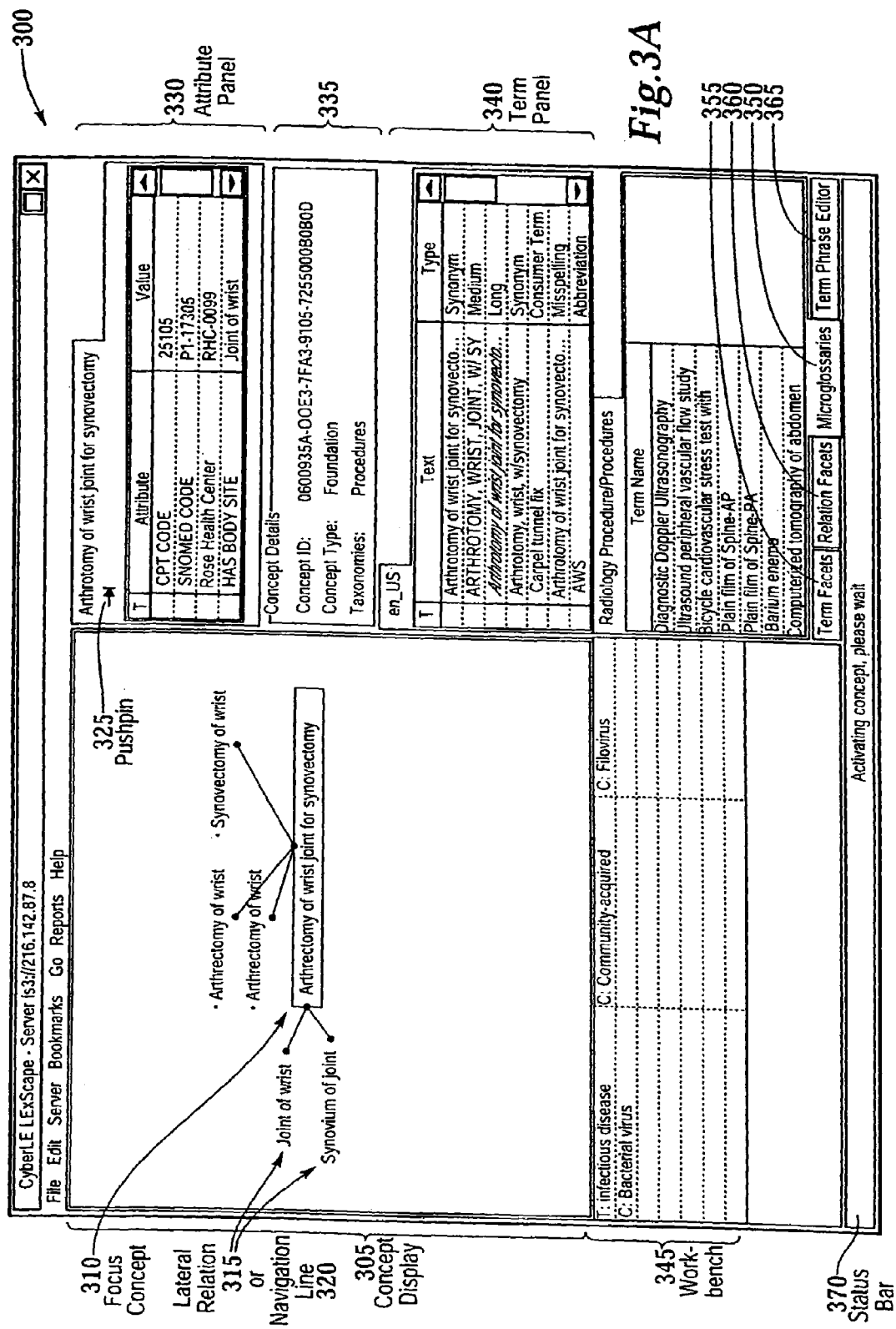
FIG. 3A depicts an illustration of a LExScape graphical user interface display in accordance with the present invention.
Figure 3B:
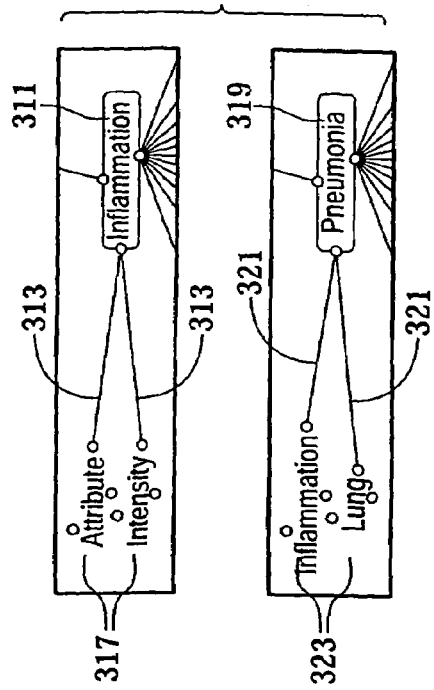
FIG. 3B depicts an illustration of a LExScape graphical user interface display representing an enlarged view of focus concept 310, lateral relation 315 and navigation line 320 from FIG. 3A in accordance with the present invention.

FIG. 3B depicts an illustration of a LExScape graphical user interface display representing an enlarged view of focus concept 310, lateral relation 315 and navigation line 320 from FIG. 3A in accordance with the present invention. Focus concept 311 is laterally related to concepts 317. This relationship is depicted by lines 313. Lines 313 are also navigation lines. Focus concept 311 can also have lateral relationships that can be viewed from a different perspective. Focus concept 311 becomes one of concepts 323 when focus concept 319 is selected. Lines 321 indicate the lateral relationship, as well as functioning as navigation lines.

Before the user can create and modify such object values as concepts, facets, relations and microglossaries, the user must first define the objects. The present invention provides many predefined objects such as concept type, relation definition, facet definition and microglossary definition. When the user begins adding objects and values by adding new concepts and facets, the first step is to decide the type of object or value to be added. To view a list of predefined object types, the user selects the appropriate "Edit [object type] Definitions" in the "Edit" selection from the menu bar at the top of the main GUI display as shown in FIG. 3. For example, if the user wants to see a list of relation types, the appropriate selection would be "Edit Relation Definitions." The list appears as part of a dialog box that also allows the user to create new objects, delete objects and edit objects.

In addition, a user can open multiple main windows at one time. A new window is opened by selecting the "New Window" entry from the File menu, or by pressing a button on the toolbar. The new window is initially focused on the concept that was the focus concept of the window from which the "new window" operation was performed. Each window may be navigated independently. Drag and drop operations work between main windows. Using "side by side" windows dramatically simplifies the creation of lateral maps between concept types.

Figure 4:
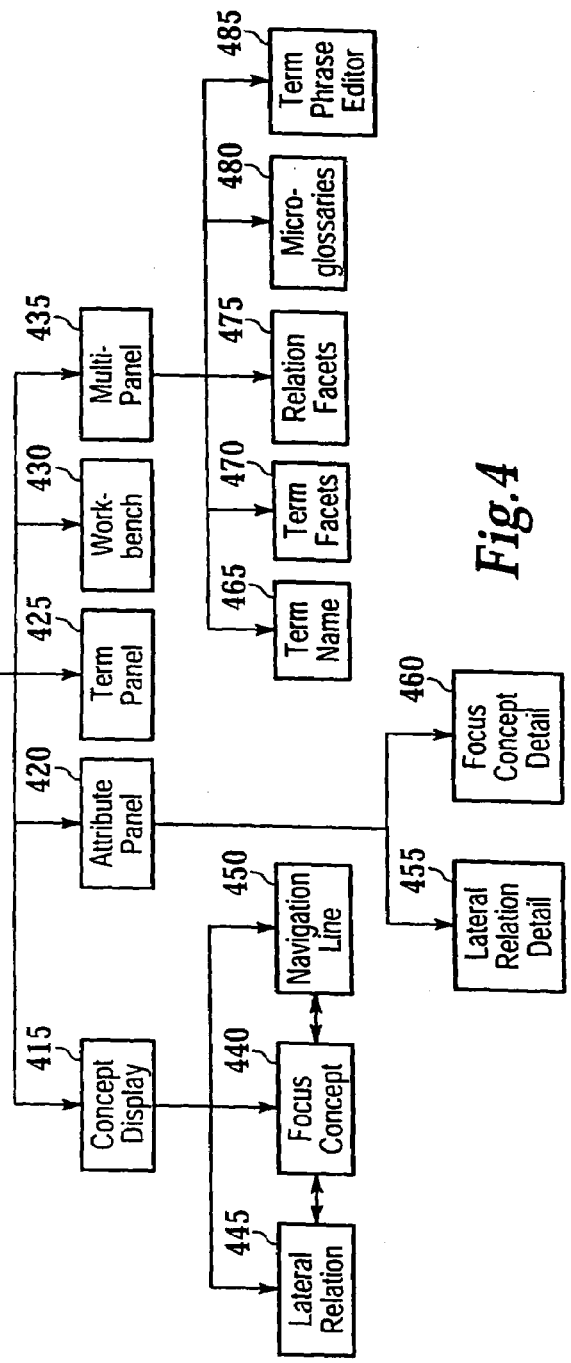
FIG. 4 depicts an illustrative diagram of an overall system in accordance with the present invention.

FIG. 4 depicts an illustrative diagram of an overall system in accordance with the present invention. The user logs-on in block 405. The main display appears in block 410. The user can then view concept display 415, attribute panel 420, term panel 425, workbench 430 and multi-panel 435. Contained within concept display 415 is focus concept 440 and any types of associations related to focus concept 440 such as lateral relation 445 and/or navigation line 450. From attribute panel 420, the user can view lateral relation detail 455 and focus concept detail 460. Term panel 425 allows the user to access terms for manipulations as described herein. Workbench 430 allows the user to temporarily store concepts and/or terms while working on them as described herein. Multi-panel 435 lists term name 465 as well as term facets tab 470, relation facets tab 475, microglossaries tab 480 and term phrase editor 485. Specific functions of each of these tabs is described in greater detail herein.

Figure 5:
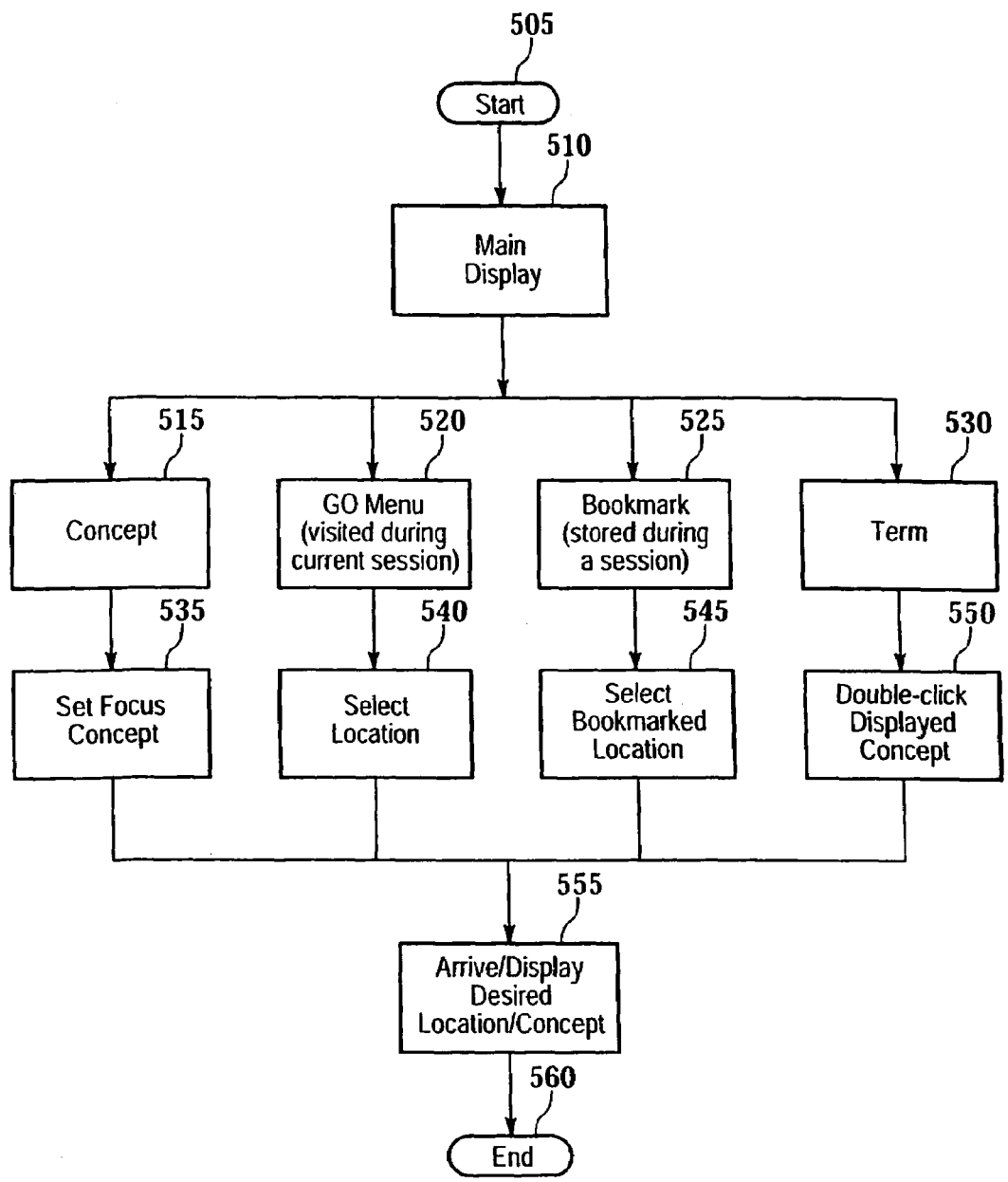
FIG. 5 depicts a flow diagram of general navigation in accordance with the present invention.

FIG. 5 depicts a flow diagram of general navigation in accordance with the present invention. Navigation begins in start terminal 505 at the main display in block 510. From the main display in block 510, the user can opt to navigate by concept in block 515, setting the focus concept in block 535 which then displays information related to that concept in block 555. Alternatively, the user can navigate through the GO menu of block 520. The user selects the location in block 540 from the GO menu list. The system then takes the user to that location in block 555. Additionally, the user can navigate through the use of previously stored bookmarks in block 525. The user selects the bookmarked location in block 545 and the system takes the user to that location in block 555. Finally, the user can navigate through the use of terms in block 530. By double-clicking on the displayed concept (designated by term) in block 550, the user selects the desired concept. The system then displays information related to that concept in block 555. Navigation ends in terminal 560.

There are several navigation methods that may be employed: the concept display, the GO menu, bookmarking or by term. Each of these methods can be easily accessed through the main GUI display as exemplified by FIG. 3. Additionally, the present invention provides methods of temporary linking multiple aspects together for easy access through the usage of a "pushpin." The pushpin enables the user to retain concept, term facet and relation facet panels by stacking multiple panels of the same kind for comparison purposes.

Navigation through the concept display is accomplished by clicking on the concept as shown in the main GUI display as shown in FIG. 3. The new concept then becomes the focus concept. A focus concept can indicate, through the use of colors, its relationship to other concepts (i.e., parents, children, and facets). For example, the display of a blue background when the mouse cursor is placed over a focus concept can indicate that the concept has children. A green background could indicate that the focus concept is a "leaf concept" (i.e. one that has no children).

Navigation through the use of the GO menu is accomplished by selecting "GO" from the menu bar at the top of the main GUI display as shown in FIG. 3. This functions in a manner similar to a WEB browser. The "GO" menu item "remembers" the locations within the concepts that the user has accessed and displays these locations in a list. The user can select the desired location from the list and will then be returned to that location. The "GO" menu item is reset when the user returns to the top-level concept.

Navigation through the use of bookmarks is a two-step process. First, the bookmark must be set. This can be accomplished in a variety of ways. The first way is by right-clicking the desired concept and then selecting "Bookmark this Concept" from the menu that is displayed. The second way is by navigating to the concept and then selecting "Bookmark" from the "Bookmarks" menu item on the main GUI screen as displayed in FIG. 3. Alternatively, the user can select a concept and then click the "Bookmark" icon on the toolbar as shown on the main GUI screen of FIG. 3. To return to a desired concept, the user can select the "Bookmarks" menu item from the main GUI screen as shown in FIG. 3. This also functions in a manner similar to a WEB browser. A list of bookmarks will be displayed, from which the user can select the desired concept in order to navigate to that concept. By double-clicking a concept listed in attribute panel 330, term panel 340, search results or a microglossary, the user can be navigated to the desired concept.

Figure 6B:
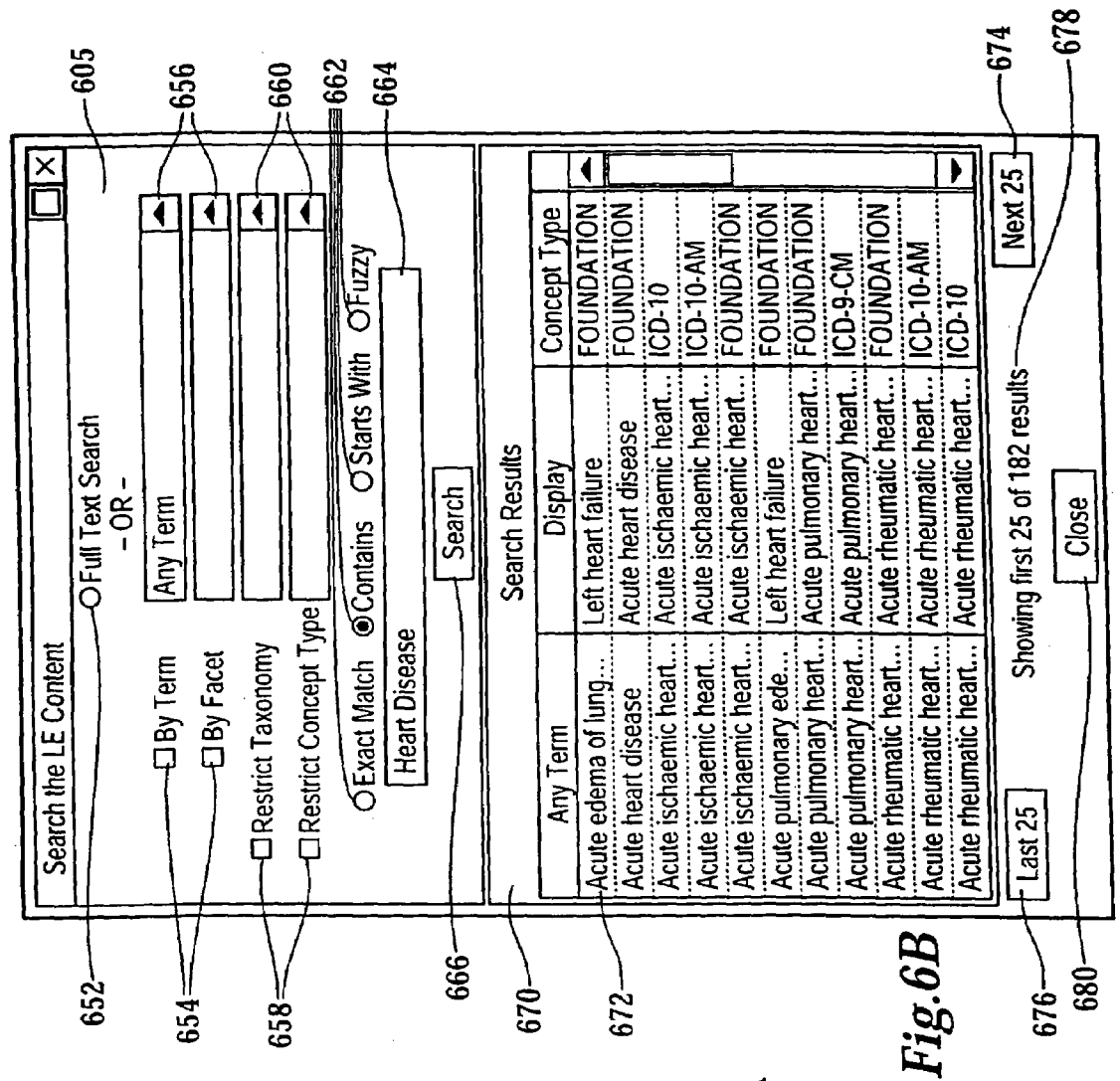
FIG. 6B depicts an illustration of a LExScape graphical user interface display representing a search screen with results in accordance with the present invention.
Figure 6A:
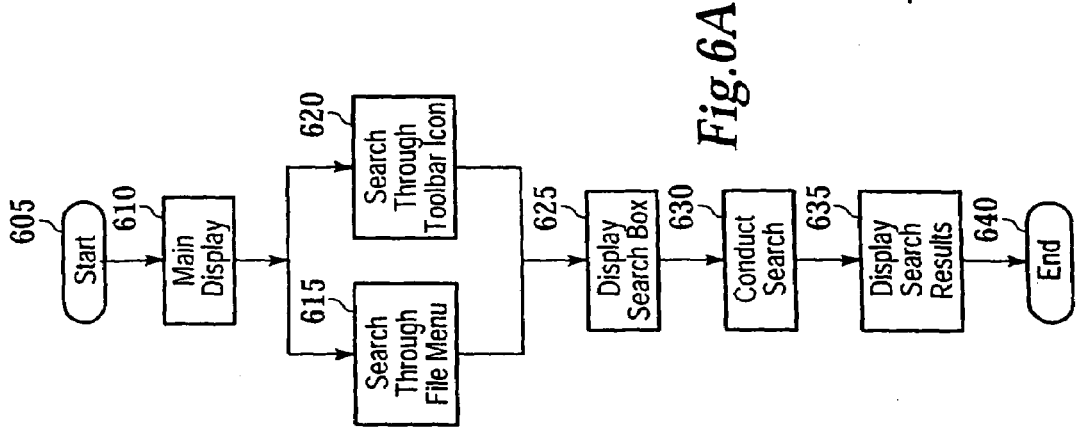
FIG. 6A depicts a flow diagram of searching in accordance with the present invention.

FIG. 6 depicts a flow diagram of searching in accordance with the present invention. The search begins in terminal 605 at the main display in block 610. The user can search through the file menu in block 615 or through the toolbar icon in block 620. The system displays a search dialog box in block 625. The user then enters search criteria and conducts the search in block 630. The system displays the search results in block 635. The user can also navigate by using these results as described herein. The search ends in terminal 640.

Searches can be performed in a variety of ways, such as exact match, contains and fuzzy search. Searches can be restricted by taxonomy or concept type. There are two (2) ways to access the search function. First, the user can select "Search" from the "File" menu item as shown in the GUI display of FIG. 3. Alternatively, the user can select the "Search" icon from the toolbar as shown in the GUI display of FIG. 3. Either of these methods opens the search dialog box.

The search dialog box allows the user to conduct a full text search or a search by term or by facet. Drop down selection boxes display lists of available terms or facets, depending on the type of search selected. The user can also select whether to restrict either the taxonomy or the concept type. Additionally, the user can choose the type of search methods from such options as: exact match; contains; starts with; and fuzzy. A text box enables the user to conduct searches on keywords not specifically found in either the term or facet drop down selection boxes. A full text type search is also available; this option implicitly inserts the "and/or" operators between all terms entered in the text box. Search results are returned in groups of 25 in alphabetical order by default. Other types of sorts and groupings may alternatively be used. A user can also navigate by using the search results. For example, by double-clicking on a returned result, the user can display the concept. Right-clicking on a returned result can display a menu containing options such as activate (navigate to the concept), show properties, add to exports or export now.

FIG. 6B depicts an illustration of a LExScape graphical user interface display representing a search screen with results in accordance with the present invention. Box 650 contains search criteria, such as full text 652, term 654 and facet 654 and their corresponding drop down selection boxes 656, taxonomy 658 and concept type 658 restrictions and their corresponding drop down selection boxes 660, search types exact match, contains, starts with and fuzzy 662 and text box 664. When the user selects to search by term 654 or facet 654, the corresponding drop down selection box 656 will become accessible. Term 654 and facet 654 may not both be selected at the same time; the user can only select either term 654 or facet 654. Similarly, the user cannot select to restrict by both taxonomy 658 and concept type 658 at the same time. Again, when the user selects to restrict by taxonomy 658 or concept type 658, the corresponding drop down selection box 660 will become accessible. Also, the user may only select one search type at a time from exact match, contains, starts with and fuzzy 662. The search commences when search 666 is pressed.

Search results are displayed in box 670. Each result 672 is displayed on a separate line. A result 672 can be used to navigate as previously described. The user can jump forward in the search result list by pressing next 674 and can jump backward in the search result list by pressing back 676. Line 678 displays the location of the user in the results list. The screen is closed by pressing close 680.

A taxonomy is a division of items in two ordered groups, categories, or hierarchies. Medical information, for example, can best be present within hierarchies. In the present invention, a taxonomy is a hierarchy of concepts. For example, "procedure" is a taxonomy. All the children of "procedure" are a part of that taxonomy. The top level of a taxonomy is the root concept. The root concepts of the present invention are defined by the enterprise in which it is used. For example, the root concepts for the healthcare industry are: SNOMED RT; HCPCS 2000 (HCFA Common Procedure Coding System); ICD-10 (International Statistical Classification of Disease and Related Health Problems, Tenth Revision); ICD-10 AM (International Statistical Classification of Disease and Related Health Problems, Tenth Revision Australian Modification); CPT (Physicians' Current Procedural Terminology); and ICD-9 CM (The International Classification of Diseases: $9^{th}$ Revision-Clinical Modification). Users can define new taxonomies at any level below the root level. When a user defines a new taxonomy, the user does not create a new hierarchy by giving a name to a portion of an existing hierarchy. Identifying new taxonomies can optimize searching. For example, a cardiologist doing modeling solely in the area of cardiac disease could create a taxonomy with the concept "myocardial disease" as its top-level concept. This would enable searches that are restricted to this taxonomy.

Figure 7:
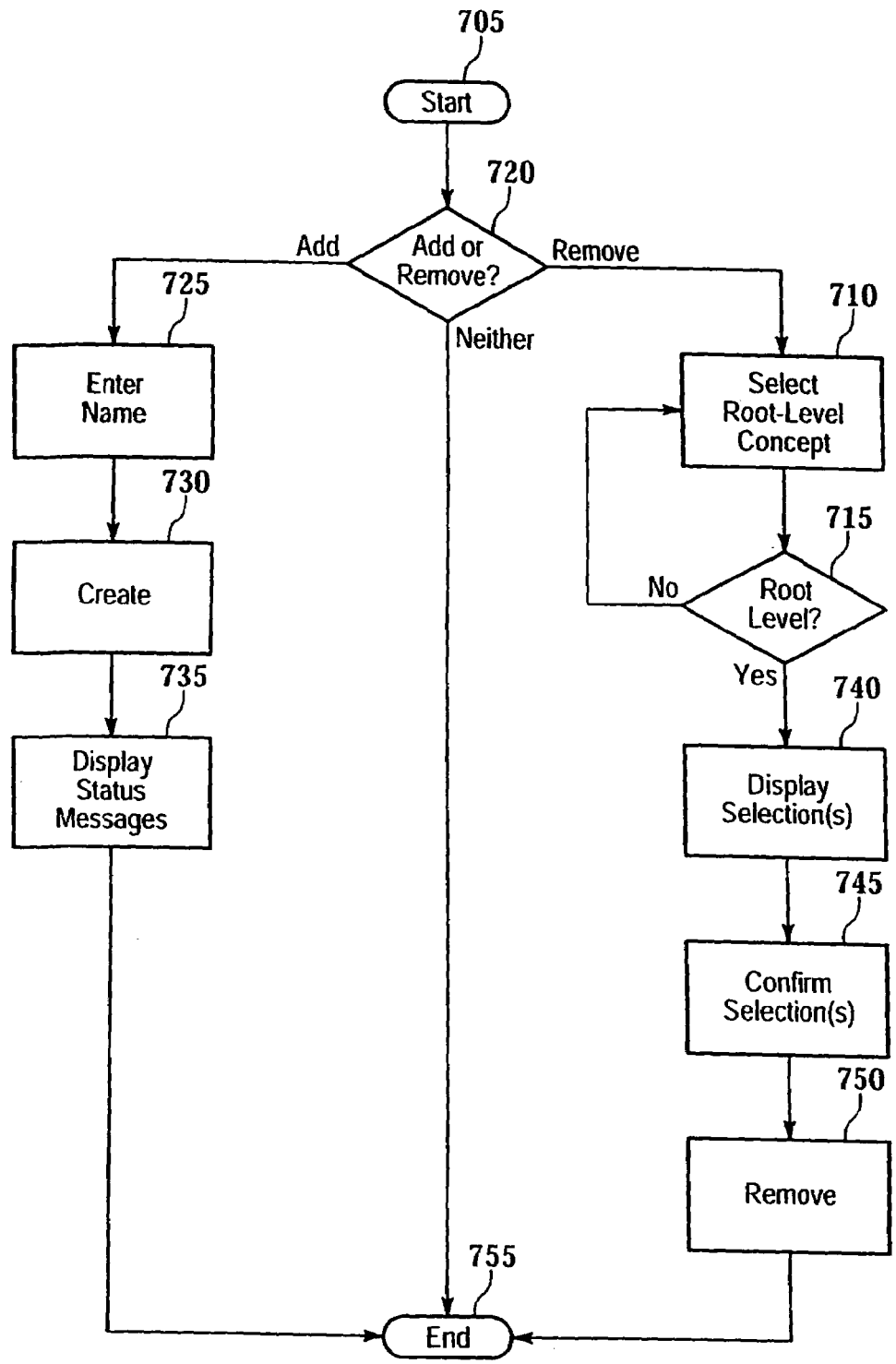
FIG. 7 depicts a flow diagram of managing taxonomies in accordance with the present invention.

FIG. 7 depicts a flow diagram of managing taxonomies in accordance with the present invention. The creation starts in terminal 705. The user has the option to either add or remove the taxonomy in decision point 720. If the user does neither, the taxonomy management flow ends in terminal 755. If the user chooses to add a taxonomy in decision point 720, the user then enters the name in block 725 and sets the system creation process into motion in block 730. The system displays status messages in block 735 during the creation process. If, however, the user chooses to remove a taxonomy in decision point 710, the user selects the root-level concept in block 710. The system then checks to verify that the user has selected a root-level concept in decision point 715. If the user has not selected a root-level concept, the user is not allowed to proceed and is returned to block 710. If, however, the user has selected a root-level concept, the system then displays the selected root-level concept selection(s) in block 740. The user then confirms their selection(s) in block 745 and sets the system removal process into motion in block 750. The taxonomy management process ends in terminal 755.

A user can create new taxonomies and delete those taxonomies that the user has created. To create a new taxonomy, the user navigates to the root-level concept under which the new taxonomy will be placed. Then, the user selects "Create Taxonomy" from the "Edit" menu item on the GUI display as shown in FIG. 3. A dialog box that allows the user to enter the name of the new taxonomy will then be displayed. After entering the name, the user selects "OK." The time it takes to create a new taxonomy will be based on the number of concepts in the custom taxonomy. Status messages may be displayed to update the user as to the progress of the creation. A status bar may also supply additional messages related to the creation. Once the new taxonomy is created, it will be displayed in the GUI screen as shown in FIG. 3.

To remove a taxonomy, the user navigates to the root-level concept of the custom taxonomy. Then, the user selects "Remove Taxonomy" from the "Edit" menu item as shown on the GUI display of FIG. 3. The present invention prevents the user from removing a taxonomy if the root-level concept has not been selected. Once the correct level has been selected, a dialog box will be displayed the selected taxonomy. Multiple taxonomies can also be selected. They will all be displayed in the dialog box. The user can then select the one or more taxonomies (thereby reconfirming the choices) for removal and select "OK."

Figure 8A:
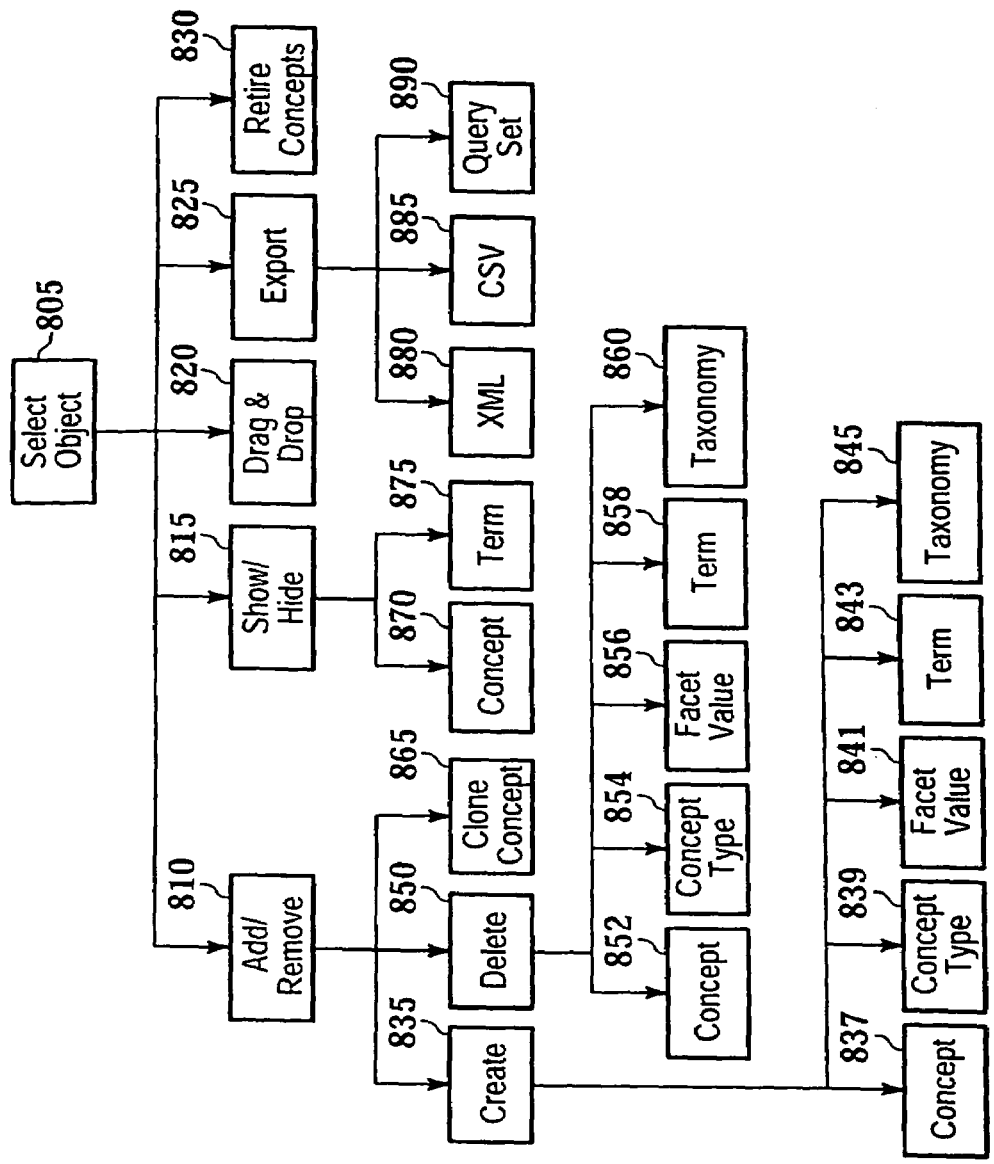
FIG. 8A depicts an illustrative diagram of manipulating information in accordance with the present invention.

FIG. 8 depicts an illustrative diagram of manipulating information in accordance with the present invention. The user selects the object to be manipulated in block 805. From there, the user can choose to add/remove in block 810, show/hide in block 815, "drag & drop" in block 820, export in block 825 and/or retire concepts in block 830. If the user chooses to add/remove in block 810, the user can further choose to create in block 835, delete in block 850 and/or clone concepts in block 865. Creating in block 835 and deleting in block 850 each operate on numerous objects. Create in block 835 allows the user to create concepts in block 837, concept types in block 839, facet values in block 841, terms in block 843 and taxonomies in block 845. Delete in block 850 allows the user to delete concepts in block 852, concept types in block 854, facet values in block 856, terms in block 858 and taxonomies in block 860. An alternative form of concept creation is to clone concepts in block 865. The user can show/hide in block 815. This operation can be performed on concepts in block 870 and/or terms in block 875. Certain objects can be "dragged & dropped" in block 820. "Drag & drop" can be used for such purposes as creating relations and formulating term phrases, as discussed herein. If the user chooses to export certain objects in block 825, the user must also choose from the available export formats, such as XML in block 880, CSV in block 885 and query sets in block 890. The user can also choose to retire concepts in block 830. Retired concepts are not removed from the system, but acquire a "read-only" type status.

The present invention enables the user to manage, export and retire concepts. Concepts can be shown or hidden. The user can clone concepts, add or remove facet values, add or remove terms, change term text, drag concepts to the workbench, include concepts on term phrases, include concepts in term lists (microglossaries), add or remove concepts, add or remove taxonomies.

Hiding or displaying concepts is accomplished by first choosing "Select Concept Type Displayability" from the "Edit" menu of the GUI display as shown in FIG. 3. This results in a listing of available Concepts and their displayability settings in various locations of the present invention. Checking a setting displays all concepts of the selected type; removing a check hides the concept.

FIG. 8B depicts an illustration of a LExScape graphical user interface display representing displayability settings in accordance with the present invention. Column 872 contains all of the concept types saved in the system. Columns 874, 876 and 878 contain settings for individual components. For example, selecting a checkbox under column 878 indicates that the associated concept type should be included in search results, such as those displayed in box 670 of FIG. 6. Additionally, selecting a checkbox under column 876 allows the associated concept type to be visible in attribute panel 330 of FIG. 3. Selecting a checkbox under column 874 allows the associated concept type to be visible in concept display 305 of FIG. 3. Deselecting a checkbox under any column causes the associated concept type to be hidden in the related location. Alternatively, selecting a checkbox could hide the associated concept type, while deselecting could show it. Checkboxes are merely one illustrative method of indicating a selection. Other methods, such as Y/N, H/S and radio buttons may also be used.

To create a new concept, the user navigates to the concept under which the new concept will be placed. The user then selects "Create Child Concept" from the "Edit" menu of the GUI display as shown in FIG. 3. This causes a dialog box to be displayed in which the user can enter the new concept name, set its facets and view its type. The child inherits the type from the parent. The user then selects "OK" and the new concept is created.

An alternative method for creating concepts is by cloning. This is accomplished by navigating to the concept to be cloned and making it the focus concept. The user then selects "Clone Concept" from the "Edit" menu of the GUI display as shown in FIG. 3. This displays a dialog box containing the concept being cloned and allowing the user to enter a name for the new concept. The type is also shown, but again is unmodifiable. The user then selects "OK" and the new concept is cloned from the existing concept.

New concept types can also be created. This is accomplished by selecting "Edit Concept Types" from the "Edit" menu of the GUI display as shown in FIG. 3. A dialog box is displayed, listing available concept types available for modifications and deletions and containing an option for creating a new concept type. The selection of the "New" option results in another dialog box. The user then can enter a new concept type name, a nickname and a description. If the new concept type name is not entered, the nickname will be used for display purposes. In this case, the nickname will be required. Alternatively, if the nickname is not entered, the new concept type name can be used in its place. In this case, the new concept type name will be required. The description is also optionally, but can be made mandatory. Selection of the "OK" button returns the user to dialog box containing the listing of available concept types. Selecting "OK" on this dialog box returns the user to the GUI display as shown in FIG. 3.

FIG. 8C depicts an illustration of a LExScape graphical user interface display representing a definition editor in accordance with the present invention. Similar editors may be used for concepts, relations, facets, concept types and taxonomies. Box 836 is a unique identifier assigned by the system. Box 838 is a text box for entering a name identifier. If entry is required in box 838, then the entry must be unique. Box 840 is a text box for entering a nickname. If entry is not required in box 838, then it will be required in box 840. The converse is also true. If entry is required in box 840, then the entry must be unique. Box 842 is a text box for entering a description of the entered object. Box 842 may be either optional or mandatory.

A concept's properties can also be viewed and added. This can be accomplished by right-clicking the desired concept. The resultant menu displays such options as: show concept properties and add concept properties.

Concepts and their associated facets can also be exported into such formats as XML (extensible Markup Language), a query set and CSV (comma-separated values). This is accomplished by navigating to the concept, right-clicking on it and selecting either "Mark for Export" or "Export Now" from the resultant menu. The first selection adds the concept to a list of concepts to be exported. This list can be accessed by selecting "Concept Export Manager" from the "File" menu of the GUI display as shown in FIG. 3. This displays a dialog box containing selected concepts and their relations and descendents. The second selection adds the concept to a list of concepts to be exported and immediately commences the export procedure by displaying the dialog box containing selected concepts and their relations and descendents. The Export Manager can also be invoked from a button on the toolbar.

In this dialog box, the user has the option of deselecting the concept(s) and/or their relations and/or descendents. The user can further refine the export by selecting the "Enable Export Filters" option. This allows the user to include or exclude concepts based on facets. Any number of filters can be used. After making selections, the user clicks "Next." The procedure then differs based on whether or not filters have been enabled.

If filters have been enabled, a dialog box is displayed allowing the user to define and add filters based on facets. Various types of filters can be used, such as "include-if-present" and "exclude-if-present." Selecting "Next" resumes the basic export procedure.

At this point, the user is allowed to select the format into which the concepts will be exported. Again, the user selects "Next" to continue the export procedure. A dialog box is then displayed allowing the user to perform a variety of export-related functions such as specifying the export destination (for example, exporting to a new file or appending to an existing file) and testing the export. It is also possible to test the export and then save it to a file. Clicking "Finish" completes the export. The export may also be halted by selecting "Stop the Export." If the user selects CSV format, they may then select specific facets to be included as columns in the export. This option is not available for XML format since XML format contains all information on the concept being exported.

A concept that has been retired, has been removed from use but is still in the system. Retired concepts can be cloned, displayed or hidden. They may also be "unretired." However, terms, facets or relations cannot be added to retired concepts. All of the descendents of a concept selected to be retired must also be retired or moved to become the children of other concepts before a concept can be retired. Additionally, when a concept is retired, its terms are also retired.

To retire a concept, the user navigates to the concept and right-clicks on it. Then, the user selects "Retire Concept"

from the resultant menu. A confirmation box is then displayed. The user clicks "OK" to retired the concept. When displayed, retired concepts can be visually designated by such means as a special symbol.

Figure 9:
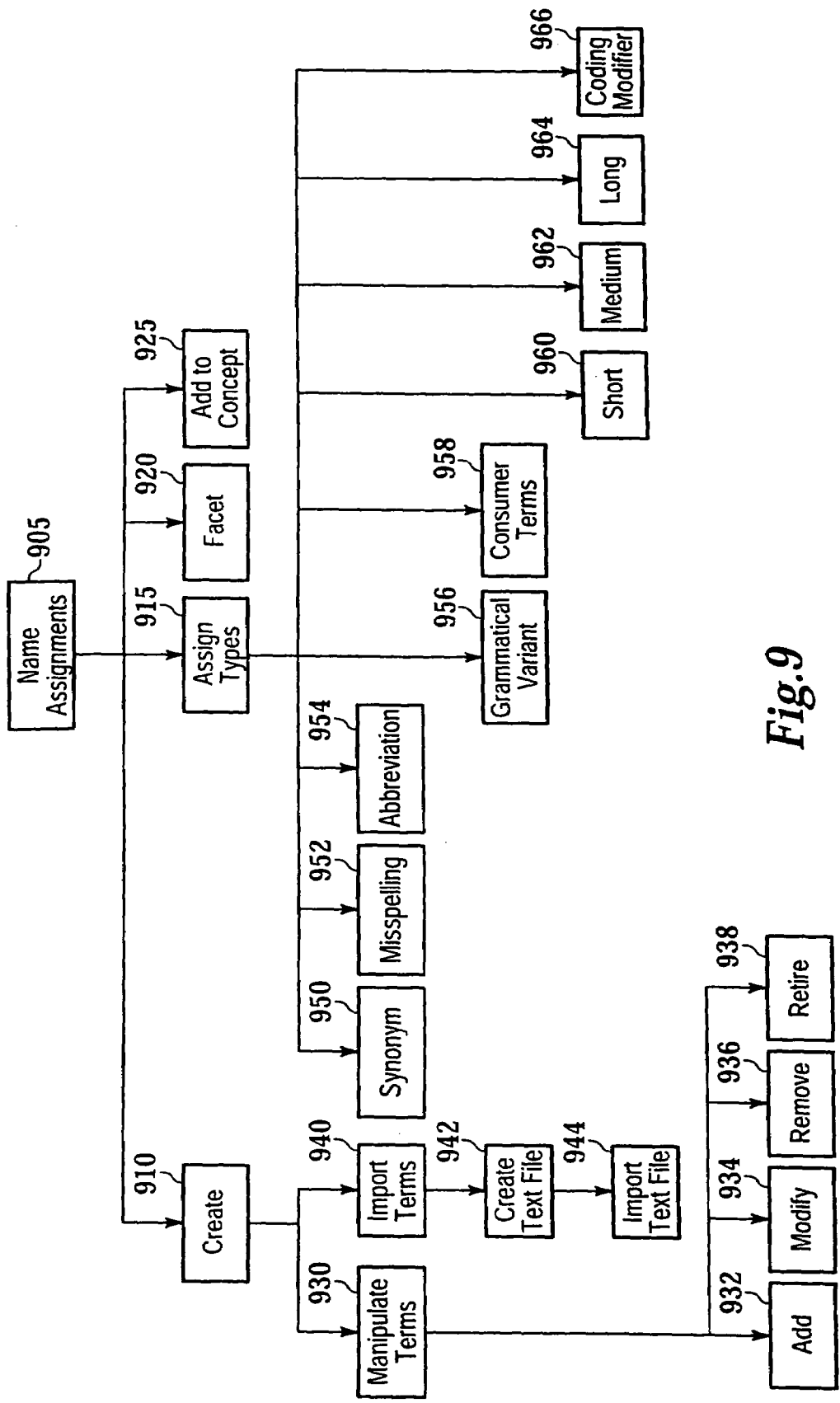
FIG. 9 depicts an illustrative diagram of name assignments in accordance with the present invention.

FIG. 9 depicts an illustrative diagram of name assignments in accordance with the present invention. The user commences a name assignment process in block 905. The user can choose to create in block 910, assign types in block 915, manage facets in block 920 or add a name to a concept in block 925. If the user chooses to create in block 910, the user can do so by either manipulating current terms in block 930 or importing terms in block 940. Manipulating terms in block 930 can further be broken down into the actions of adding in block 932, modifying in block 934, removing in block 936 and retiring in block 938. Before importing terms in block 940, the user must have or have created a text file containing those terms in block 942. Once the text files exists, the user can then import it in block 944. There are a number of types that can be assigned in block 915. These are, for example: synonym in block 950, misspelling in block 952, abbreviation in block 954, grammatical variant in block 956, consumer terms in block 958, short in block 960, medium in block 962, long in block 964 and coding modifiers in block 966. These are discussed in greater detail herein.

Terms give names to concepts. When creating a concept, the user must assign it at least one term so that the concept can have a display term. After a concept has been created, the user can add new terms to it, retire outdated terms, change a term's type and reassign the display term. As with retired concepts, retired terms can also be shown or hidden. Terms can be used to build term lists, also known as microglossaries. Terms have facets and types. Term facets enable the user to link codes or other data to terms in the same manner that concept facets link associated data with concepts.

There are a variety of term types, such as: synonym (for example, asthma), misspelling (for example, azma for asthma), abbreviation (for example MI for myocardial infarction), grammatical variant (for example reddish as a variant of red), consumer term (for example, heart attack for myocardial infarction), short (for example, exploratory heart surgery), medium (for example, cardiotomy, exploratory w/removal, FB; w/o bypass), long (exploratory heart surgery with removal of foreign body; without bypass), coding modifier (external upper lip). Coding modifiers represent a portion of a diagnosis, procedure, or other entity. They are used in a coding system to reduce text by omitting the common part of a statement that would be repeated for a series of codes. For example, one group of coding modifiers from the ICD-10 series lists various areas of a lip (C00.0-.9). Use of one of these coding modifiers also assumes the inclusion of the text from code C00 which is "malignant neoplasm of lip."

The present invention allows the user to import lists of words that can be used as terms. By creating a plain text file of these words and importing the file into the present invention through the "Import Term Candidates" option on the "File" menu of the GUI display as shown in FIG. 3. Once imported, these words appear on the workbench as shown in the GUI display of FIG. 3.

To add a new term to a concept, the user navigates to the concept and right-clicks on it. From the resultant menu, the user then selects "Add Term." A dialog box is then displayed enabling the user to enter the new term and select its type. The present invention checks to ensure that no identical active term exists for this concept in the current locale. If the term is unique, it is assigned and appears in the term panel for that concept.

To change a term type, the user right-clicks on the term and selects "Change Term Type" from the resultant menu (Terms may also be added, replaced and retired from the same menu.). A type list dialog box appears from which the user can select the new type. The change is completed when the user selects "Change" from the dialog box.

The display term for a concept can be changed if the concept has more than one term assigned to it. This is accomplished by right-clicking the term that will become the new display term and selecting "Make Display Term" from the resultant menu (This menu also allows the user to add terms, retire and replace terms, retire terms, change term type and access properties.). The present invention requests confirmation of the desired action. Selecting "Yes" completes the action.

Figure 10A:
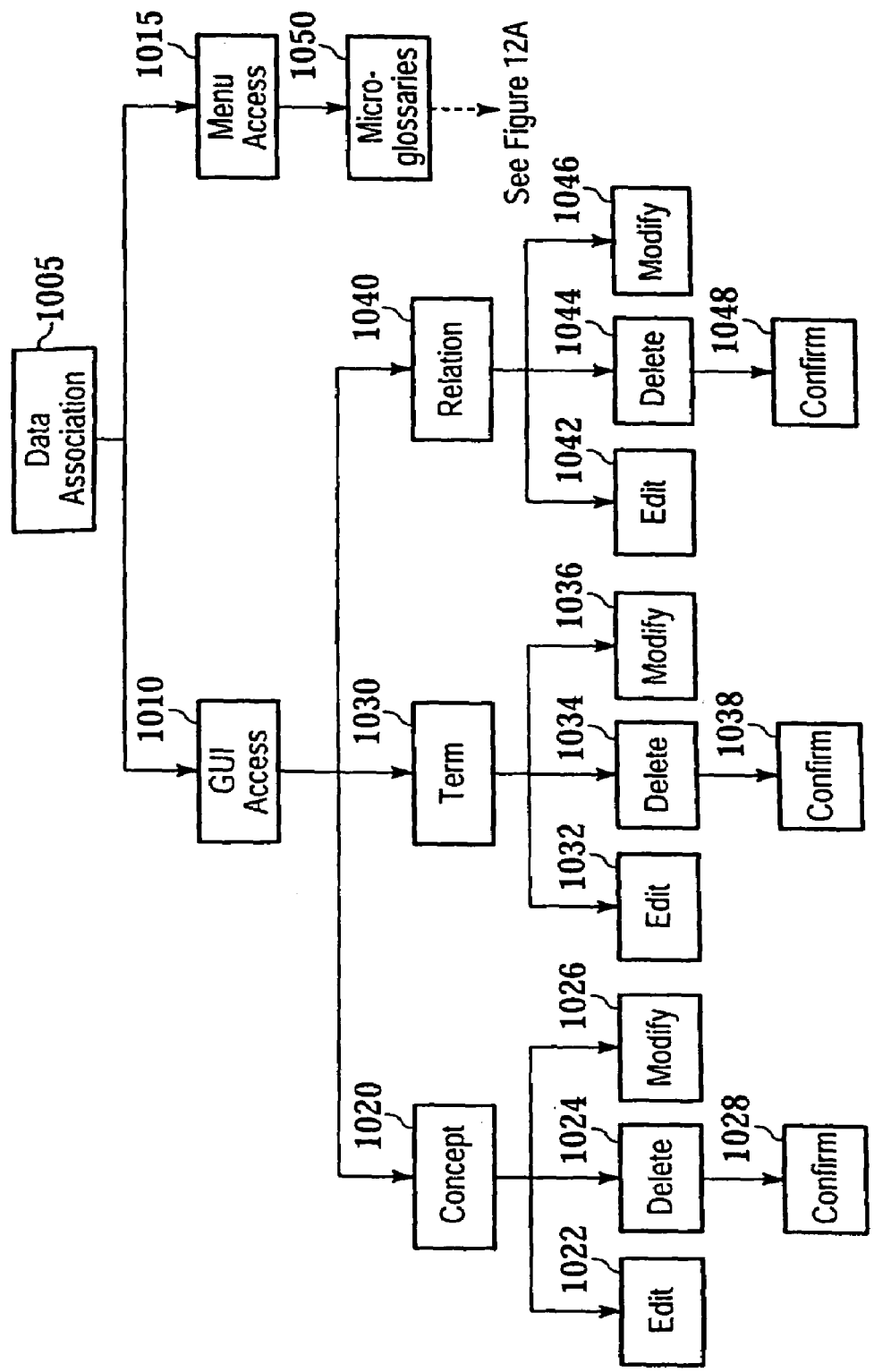
FIG. 10A depicts an illustrative diagram of data association in accordance the present invention.

FIG. 10A depicts an illustrative diagram of data association in accordance with the present invention. The user commences a data association process in block 1005. This process can be performed either through GUI access in block 1010 or menu access in block 1015. GUI access in block 1010 allows the user to work with concepts in block 1020, terms in block 1030 or relations in block 1040. For each of these objects, the user can edit (blocks 1022, 1032 and 1042, respectively), delete and confirm (blocks 1024 and 1028, 1024 and 1038, and 1044 and 1048, respectively) and modify (blocks 1026, 1036, and 1046, respectively). Menu access in block 1015 allows the user to perform data associations for microglossaries in block 1050. Microglossories and the associated actions performed upon them will be described in greater detail in relation to FIG. 12 herein.

Facets store values associated with concepts, terms, relations, microglossaries and microglossary entries. Facets have a variety of attributes, among them mentioned versus inherited, cardinality and inheritability. Facet values are "mentioned" only once. This is as related to the first concept to which it is added. Facet values can be inherited many times. If the facet is defined as inheritable, changes made to facet values on the concept where the facet value is mentioned affect not only the mentioned facet values, but also their descendents. Cardinality determines whether a facet can have only one, or multiple values of a particular facet on any given concept or term. Inheritability determines whether facet values are inherited by the concept's descendents.

Some facets store coding systems such as MeSH and LOINC. Others store information that will be used by external applications. For the healthcare industry, coding systems such as LOINC, MedicineNet, MeSH and UMLS, are stored in facets. Facets can be created, changed and deleted. Concept facets, term facets and relation facets are accessible from the GUI display as shown in FIG. 3. Two (2) types of microglossary facets currently are available: those associated with the entire microglossary, and those associated with entries in the microglossary. Microglossary facets are accessed by selecting the "Microglossary Manager" from the "File" menu of the GUI display as shown in FIG. 3. Microglossaries will be discussed in greater detail in relation to FIG. 12.

To manage facet definitions, the user selects "Edit Facet Definitions" from the "Edit" menu of the GUI display as shown in FIG. 3. A facet management dialog box is displayed, listing all existing facet definitions and allowing the user to edit, create and delete. Selecting "New" will display a facet definition dialog box in which the user enters the facet name and/or nickname (one or the other will always be required and must be unique) and an optional, but highly useful, description. Various other facet attributes can also be set, such as type restriction, cardinality, displayability, inheritability, immutability and applicabilities (for example, term and concept). Clicking "OK" after entering and setting the facet name and attributes creates the new type of facet and closes the facet definition dialog box.

FIG. 10B depicts an illustration of a LExScape graphical user interface display representing a definition management dialog box in accordance with the present invention. Similar editors may be used for concepts, relations, facets, concept types and taxonomies. The object names are listed in column 1060. New objects can be added by pressing new 1064. Existing objects can be modified by pressing edit 1062 or deleted by pressing delete 1066. Object applicabilities are indicated in column 1068. A checkmark in 1070, 1072, 1074, 1076 and/or 1078 of any row indicates that the associated object is applied in that manner. For instance, a checkmark in 1070 of any row indicates that the associated object is applicable to terms. Or, a checkmark in 1078 indicates that the associated object is applicable to relations.

To modify an existing facet definition, the user would highlight the desired facet definition and select "Edit" on the facet management dialog box. This displays the facet definition dialog box with the data related to the selected facet definition displayed. The user can then make modifications to the facet definitions in the areas as described in relation to creating new facet definitions.

To delete an existing facet definition, the user highlights the desired facet definition and selects "Delete" on the facet management dialog box. The system then requests confirmation prior to performing the deletion.

The procedures for adding facet values to concepts, terms and relations are similar. In each case, the user must navigate to the concept, term or relation to which the facet value will be added. To add a facet value to a concept, the user right-clicks within the body of the attribute panel on the GUI display as shown in FIG. 3 (or on a row in the panel if a values are present). From the resultant menu, the user then selects "Add Facet." To add a facet value to a term or relation, selects the term or relation then clicks within the term or relations panel to access the context menu for that panel. To select a relation, the user then clicks its relation line in the concept display. Once the relation is selected, the name of the relation is displayed in the tab of the relation facets panel. To select a term, click that term in the term panel. In each case, the final result will be a dialog box listing the available facet types and a value data entry box. From the list, the user clicks the desired facet type and enters the facet's value. Finally, the user clicks "Add" and the new facet value is displayed as related to the concept, term or relation that the user selected.

Facet values can also be modified and/or deleted. To modify a facet value, the user right-clicks the facet value in the attribute or term panel of the GUI display as shown in FIG. 3. The user then selects "Edit Facet Value" from the resultant menu. A dialog box will then appear allowing the user to enter and new value for the facet. Clicking "Change" completes the process. To delete a facet value, the user right-clicks on the concept, term or relation from which the facet value is to be deleted. The user then selects "Remove Facet Value" from the resultant menu. The system requests confirmation of the action prior to processing the deletion request.

FIG. 11 depicts an illustrative diagram of linking concepts in accordance with the present invention. The user commences the relations process in block 1105. The user can manage hierarchical (parent/child) relations in block 1110, lateral relations in block 1115 or create new definitions in block 1120. Parent/child relations in block 1110 can be removed by deleting the link between them in block 1139. Creation of a parent/child relation can be accomplished in two (2) ways. The user can drag the parent to the workbench in block 1127, select the child in block 1129 and drag the parent above the child in block 1131. Alternatively, the user can drag the child to the workbench in block 1133, select the parent in block 1135 and drag the child below the parent in block 1137. Lateral relations in block 1115 are created by dragging the target to the workbench in block 1145, selecting the source in block 1150, choosing the relation type in block 1149, selecting both the source and the target in block 1151, and adding the lateral relation in block 1153. Creating a new definition in block 1120 involves adding in block 1155, modifying in block 1160 and deleting in block 1165.

A concept is defined by its relations, which link two concepts. The present invention provides two (2) predefined relation types: hierarchical (parent-child) and lateral. New relations types can be created. Parent-child relations are created when new concepts are added. Existing concepts can be linked by adding new parent-child relations. This can be accomplished by adding a new parent to a child concept, or by adding a new child to a parent concept.

Figure 11A:
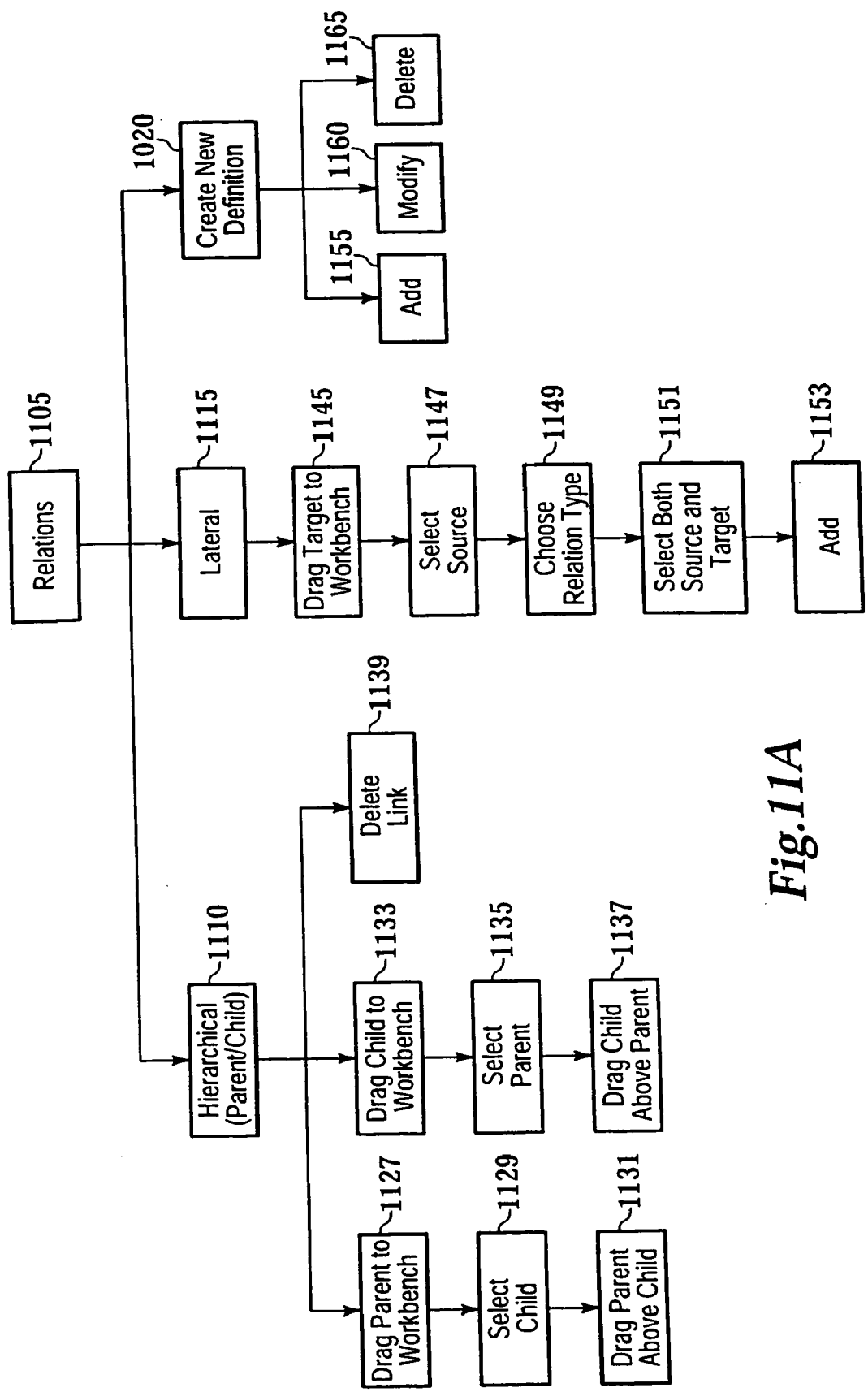
FIG. 11A depicts an illustrative diagram of linking concepts in accordance with the present invention.
Figure 11B:
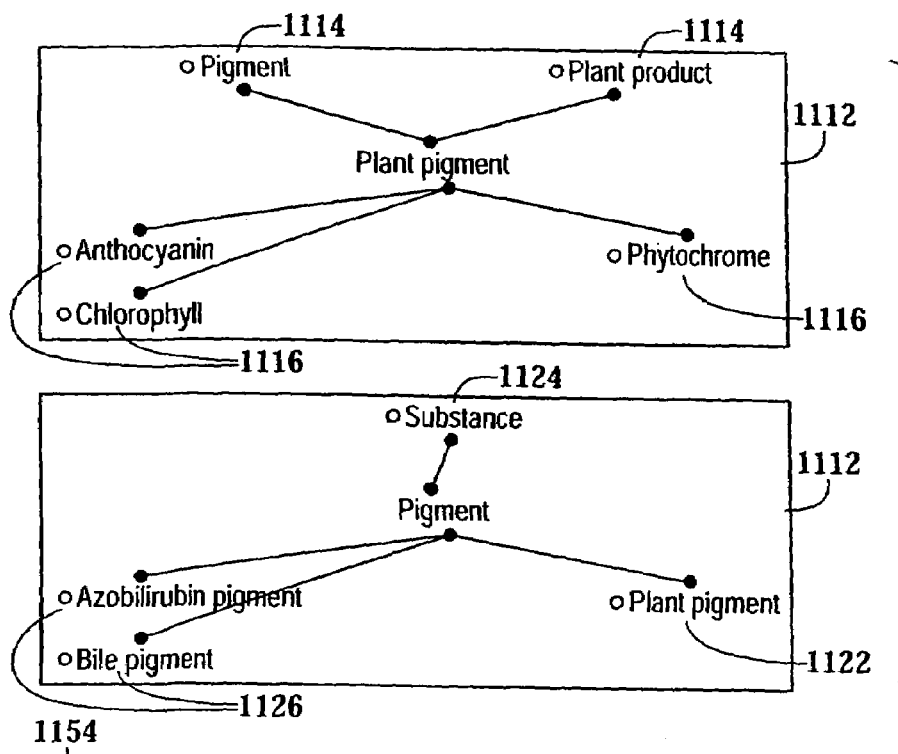
FIG. 11B depicts an illustration of a LExScape graphical user interface display representing parent/child and sibling relationship in accordance with the present invention.

FIG. 11B depicts an illustration of a LExScape graphical user interface display representing parent/child and sibling relationships in accordance with the present invention. Focus concept 1112 has two (2) parents 1114 and three (3) children 1116. To view the siblings of focus concept 1112, the user selects one of the parents 1114, making it focus concept 1124. Focus concept 1112 becomes child 1122 when parent 1114 becomes focus concept 1124. Focus concept 1112/child 1122 has two (2) siblings 1126.

The new parent cannot already exist within the child's hierarchy, either as an ancestor or a descendent. If it does, the present invention will generate a message. The message may be simply an error message or may offer an alternative action such as replacing the parent. If such an alternative is selected, inheritable properties of the new parent are added to the child concept, retaining its inheritability.

To add a parent, the user drags the concept to which the parent is to be added to the workbench on the GUI display as shown in FIG. 3. Then, the user navigates to the concept to be added as the new parent and makes it the focus concept. The user drags the child concept from the workbench to an area below the new parent in the concept display. Alternatively, the parent concept could be dragged to the workbench, the child concept made the focus concept in the concept display, and the parent concept then dragged to an area above the child concept in the concept display. To remove a parent-child link, the user clicks the link and then confirms the removal for the system.

Lateral relations are not hierarchical. They may or may not define the focus concept. The present invention represents all SNOMED RT roles as lateral relations that define the source concept. Another type of lateral relation is a code set mapping, such as that which links SNOMED RT to ICD or CPT codes, but does not define either SNOMED RT or the coding concept. Code set mappings link a concept to another concept that represents a code in a set such as CPT or ICD-10. It is useful, for example, to link a clinical concept with an administrative coding concept.

To add a lateral relation, the user navigates to the concept that will be the target of the new relation and drags the concept to the workbench on the GUI display as shown in FIG. 3. Next, the user navigates to the concept that will be the source of the new relation and right-clicks in the body of the attribute panel of the GUI display as shown in FIG. 3. From the resultant menu, the user then selects "Add Relation." A dialog box is displayed containing drop down selection boxes that list available relations and available concepts. The user selects the relation type and the concept that had been previously dragged to the workbench. Finally, the user clicks "Add" to establish the relation. A relation can also be created by dragging and dropping a concept from the workbench onto the attribute panel. In this case the add relation dialog appears, with the list of relation types already filtered down to those relation types that can legally have the focus concept as a source and the dropped concept as a target.

To create a new relation definition, the user selects "Edit Relation Definitions" from the "Edit" menu of the GUI display as shown in FIG. 3. A relation management dialog box is displayed from which the user can select a relation name and opt to add, edit or delete. Selecting "New" displays a relation definition dialog box. Again, the user will enter either or both the name and nickname (one of which will be required and must be unique) and an optional description. Various relation attributes can also be selected such as: is reciprocal, reciprocal name, type restriction, source type, target type, hierarchical, inheritance relation, cardinality, ordered, transitive, acyclic, inheritable, relationship qualifier, displayable and immutable. Once all of the desired selections have been made, the user clicks "OK" to create the new relation type. The user is then returned to the relation management dialog box.

Figure 11C:
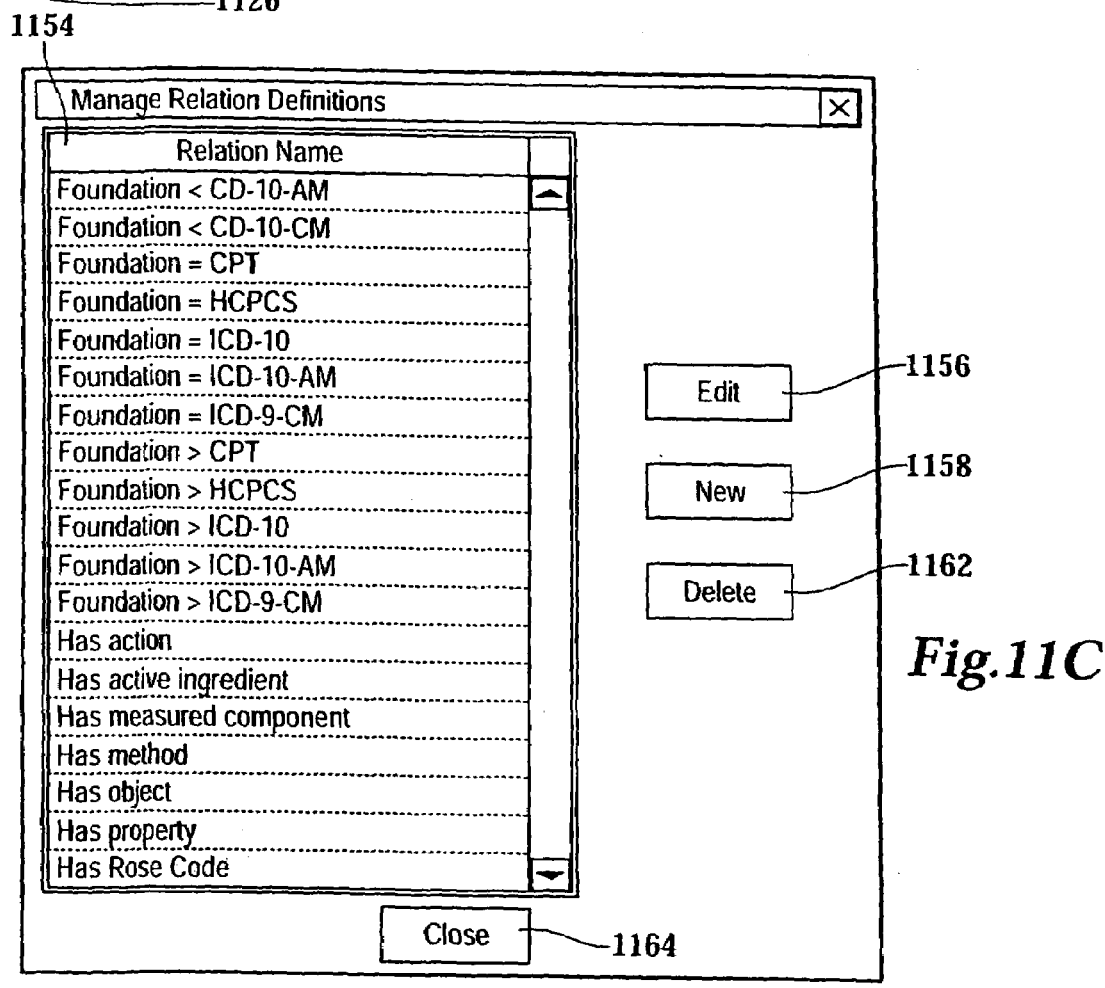
FIG. 11C depicts an illustration of a LExScape graphical user interface display representing an alternative definition management dialog box in accordance with the present invention.

FIG. 11C depicts an illustration of a LExScape graphical user interface display representing an alternative definition management dialog box in accordance with the present invention. Similar dialog boxes may be used for concepts, relations, facets, concept types and taxonomies. The object names are listed in column 1154. New objects can be added by pressing new 1158. Existing objects can be modified by pressing edit 1156 or deleted by pressing delete 162. The dialog box can be closed by pressing close 1164.

Figure 11D:
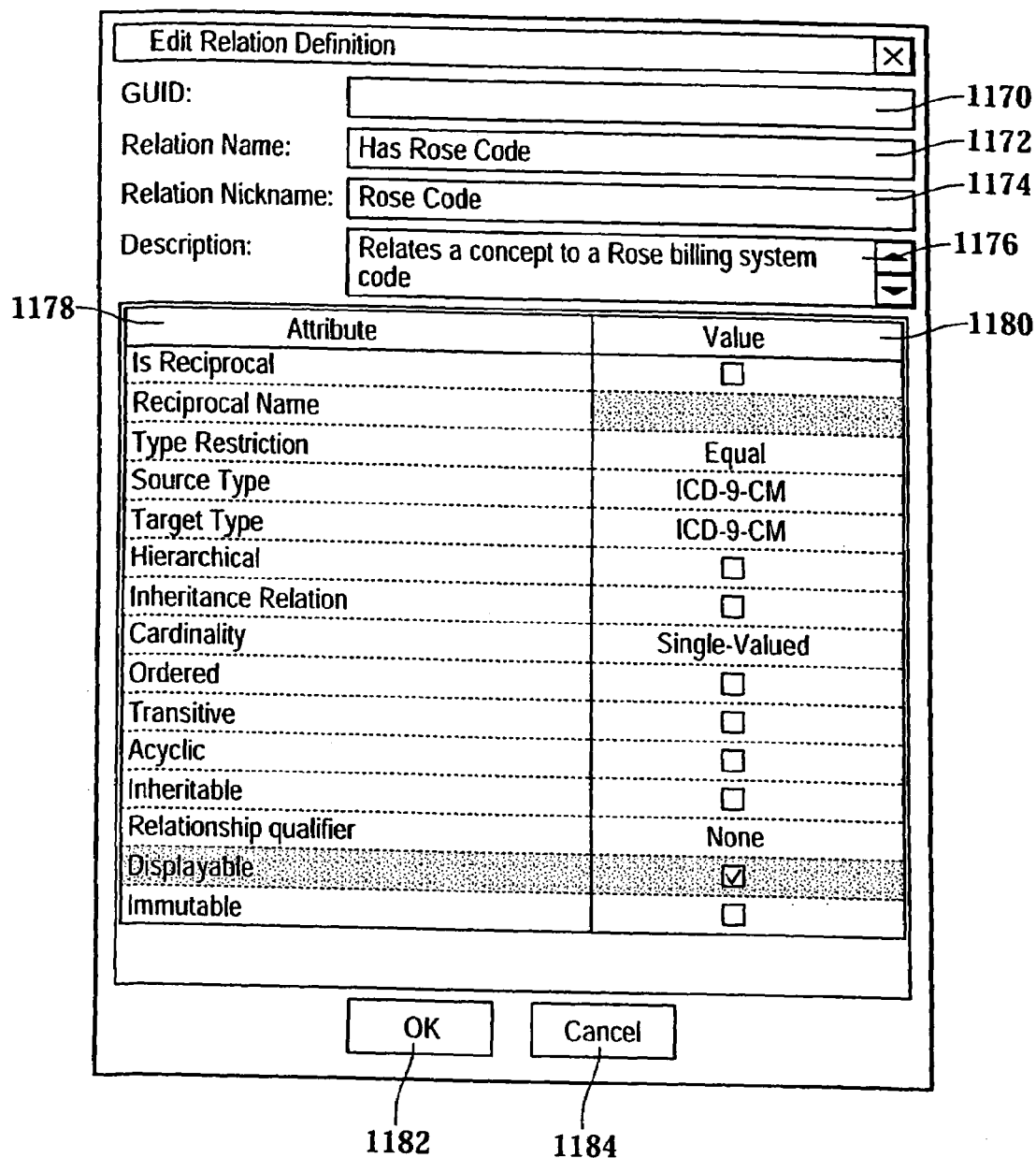
FIG. 11D depicts an illustration of a LExScape graphical user interface display representing an alternative definition editor in accordance with the present invention.

FIG. 11D depicts an illustration of a LExScape graphical user interface display representing an alternative definition editor in accordance with the present invention. Similar editors may be used for concepts, relations, facets, concept types and taxonomies. Box 1170 is a unique identifier assigned by the system. Box 1172 is a text box for entering a name identifier. If entry is required in box 1172, then the entry must be unique. Box 1174 is a text box for entering a nickname. If entry is not required in box 1172, then it will be required in box 1174. The converse is also true. If entry is required in box 1174, then the entry must be unique. Box 1176 is a text box for entering a description of the entered object. Box 1176 may be either optional or mandatory. Column 1178 lists various attributes that may be assigned to the object being defined. The values for each attribute is entered/selected in column 1180. Selecting OK 1182 creates a new object and closes the dialog box. Selecting cancel 1184 closes the dialog box, but does not create a new object.

FIG. 12 depicts an illustrative diagram of creating custom lists in accordance with the present invention. The user creates custom lists through the Microglossary Manager in block 1202. The user can edit in block 1204, create in block 1206, open in block 1208, export in block 1210, associate facets in block 1212 and/or search in block 1214. Editing in block 1204 can further be broken down into deleting in block 1216, modifying in block 1218, rearranging/reordering in block 1220 and copying in block 1222. The user can choose to delete rows in block 1224, columns in block 1226 or all in block 1228. Rearranging/reordering in block 1220 can be performed using "click & drag" in block 1230 or manually in block 1232. The user can create terms in block 1234 and term phrases in block 1236. Currently, there are two (2) methods for opening microglossaries in block 1208: double-clicking the microglossary in block 1238 and right-clicking the microglossary in block 1240. The user can export all microglossaries in block 1242, a selected group in block 1244 or an individual microglossary in block 1246. All in block 1242 and group in block 1244 create a list in block 1248. Individual in block 1246 both creates the list and automatically displays it in block 1250 wherein all export lists are viewed. The user then selects the export format and desired filters in block 1252. Then, the user sets the system export process into motion in block 1254. Facets can be associated in block 1212 to entire microglossaries in block 1256 or on an individual basis in block 1258. The user can search microglossaries in block 1214 by term in block 1260 or properties in block 1262. In either case, the user must also select the search scope in block 1264, the search type in block 1266 and enter keywords in block 1268, prior to setting the system search process into motion in block 1270.

Microglossaries are custom lists made up of terms from the present invention and may also contain user-entered values. Microglossaries are built from terms, term phrases and facets. A microglossary might contain a list of commonly used drugs, major diagnosis areas, common procedures, or even a listing of ICD concepts. Microglossaries can be used as input to other applications to create, for example, a pick list. The following actions can be performed on microglossaries: add and delete terms; add, modify and delete term phrases; copy terms among open microglossaries; associate facets with the entire microglossary; build microglossary entries (one per row) by adding terms and term phrases; associate user-defined facets with entries; display concept and term facets associated with entries; delete entries (rows in the microglossary); delete entry values; and delete entire microglossaries.

Any term from any taxonomy within the present invention can be added to a microglossary. From the GUI display as shown in FIG. 3, display terms from the concept display, terms from the term panel and selected terms and term phrases from the workbench can be added to a microglossary. The display term from search results can be added to a microglossary. Selected terms and term phrases can be added to a microglossary from another microglossary.

Term phrases are built by dragging terms onto the workbench on the GUI display as shown in FIG. 3 and then arranging them in the term phrase editor. The individual terms used to build a term phrase retain their unique identifiers that had been assigned to them by the present invention at their creation. But, a term phrase is not automatically assigned a unique identifier. However, it may be possible to create an option whereby a user may alternatively define a default setting to accomplish this task. Editing functions in the term phrase editor includes selection of multiple terms and individual terms, rearranging/reordering terms, adding terms, deleting terms. Once the desired phrase is created, the output option allows the user to send the created phrase to the workbench from which it can be dragged into one or more microglossaries.

Figure 12A:
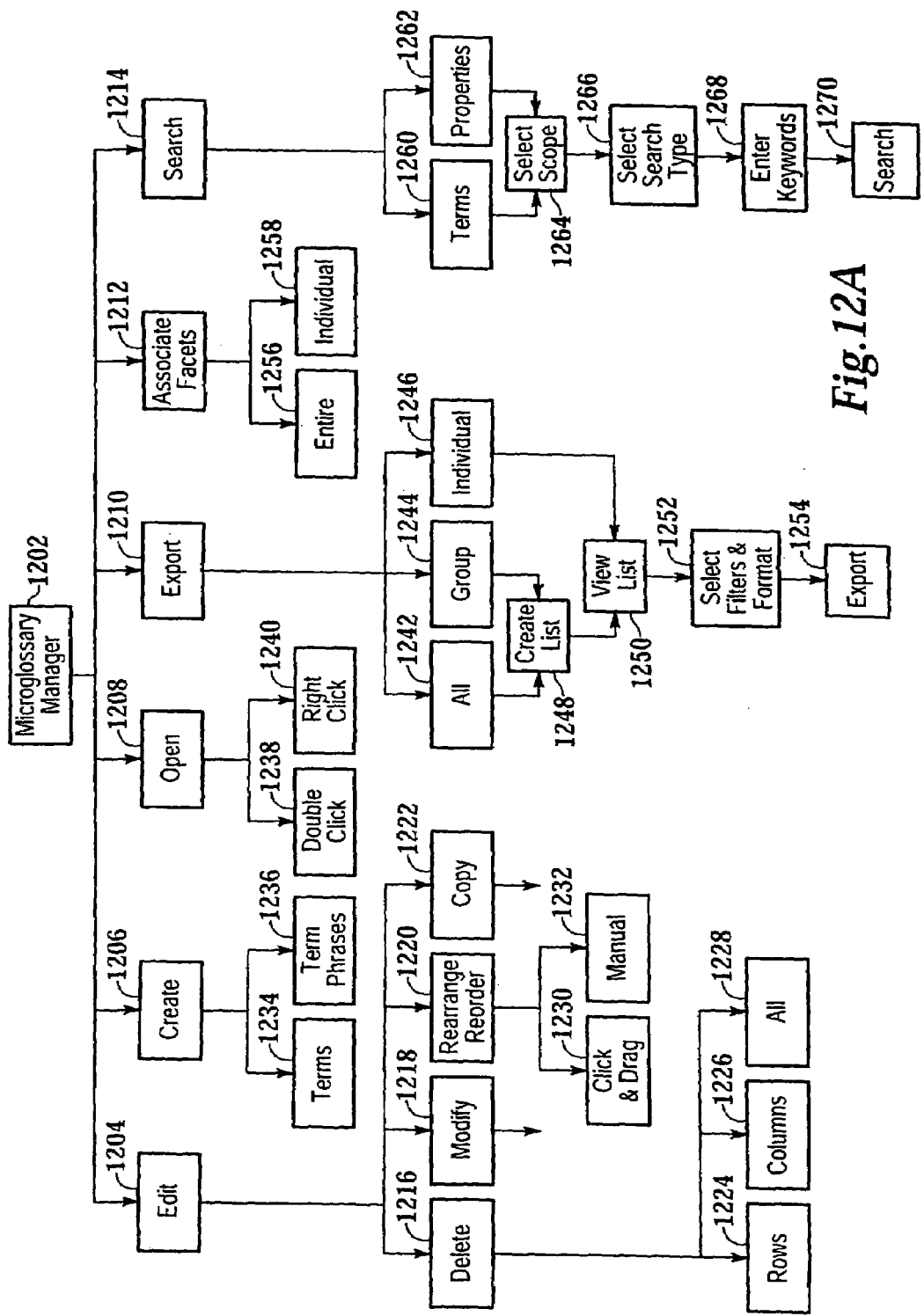
FIG. 12A depicts an illustrative diagram of creating custom lists in accordance with the present invention.
Figure 12B:
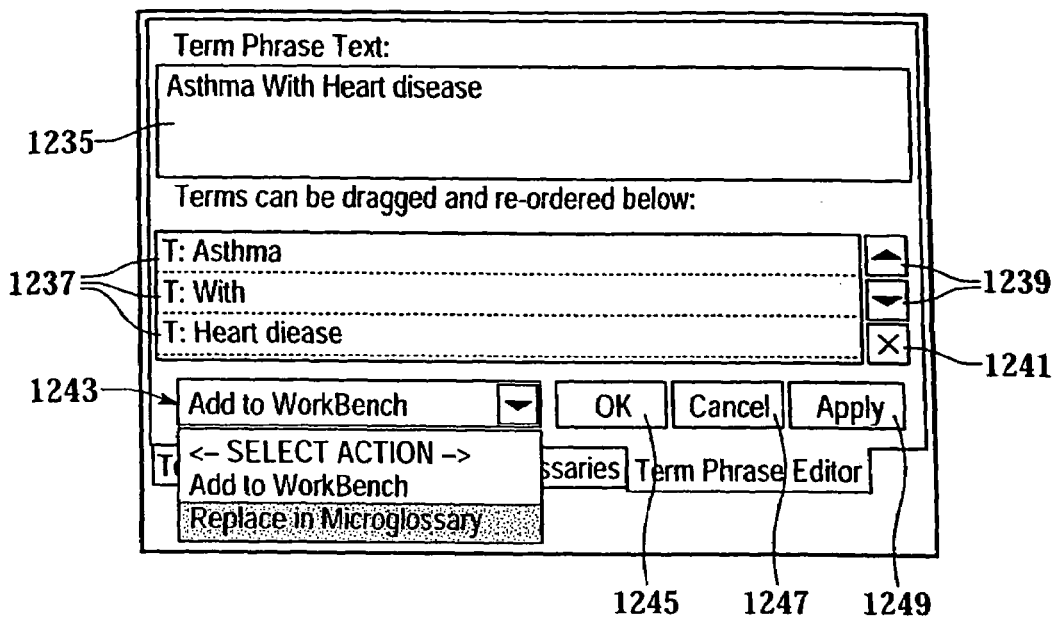
FIG. 12B depicts an illustration of a LExScape graphical user interface display representing a term phrase editor in accordance with the present invention.

FIG. 12B depicts an illustration of a LExScape graphical user interface display representing a term phrase editor in accordance with the present invention. The phrase being edited is displayed in box 1235. Terms 1237 can be dragged and reordered. Alternatively, terms 1237 can be reordered by selecting an individual term 1237 and pressing arrow keys

1239. Terms 1237 can be deleted by selecting an individual term 1237 and pressing x-key 1241. Output options 1243 determine where the destination of the phrase displayed in box 1235. Apply 1249 applies reordering, adding and deletion changes to the phrase displayed in box 1235. Cancel 1247 closes the term phrase editor without saving any changes. OK 1245 saves the changes to the location indicated by output options 1243.

All functions related to microglossaries are accessed by selecting "Microglossary Manager" from the "File" menu of the GUI display as shown in FIG. 3. The Microglossary Manager currently enables the user to view all current microglossaries, search microglossaries and manipulate microglossaries. The microglossary view may be arranged in a manner similar to the Windows Explorer system, using folders, group folders and sub-folders. Selecting a specific microglossary displays its description and its facets.

Figure 12D:
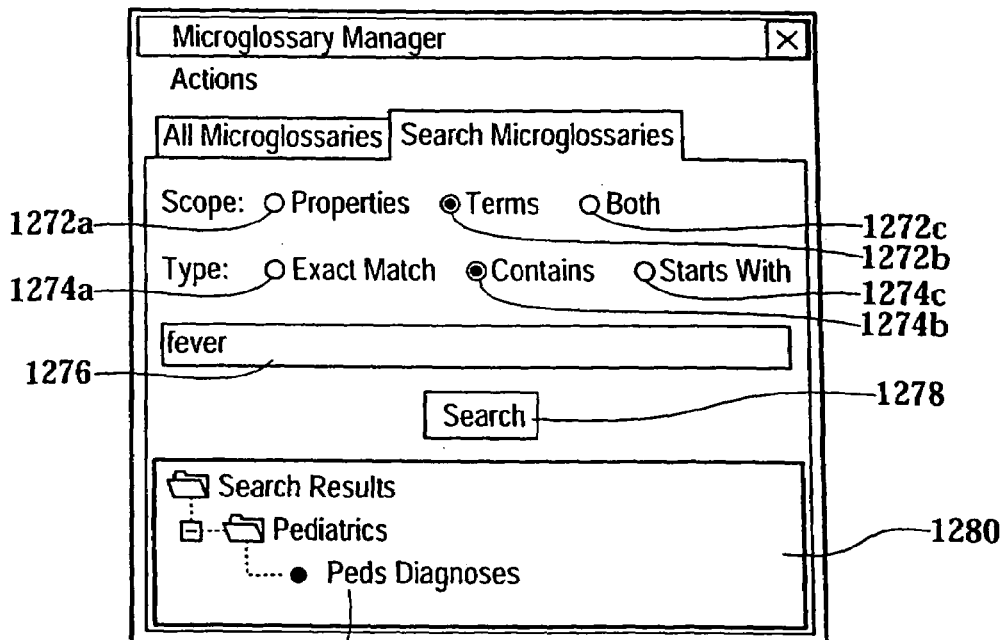
FIG. 12D depicts an illustration of a LExScape graphical user interface display representing a custom list search screen with results in accordance with the present invention.
Figure 12C:
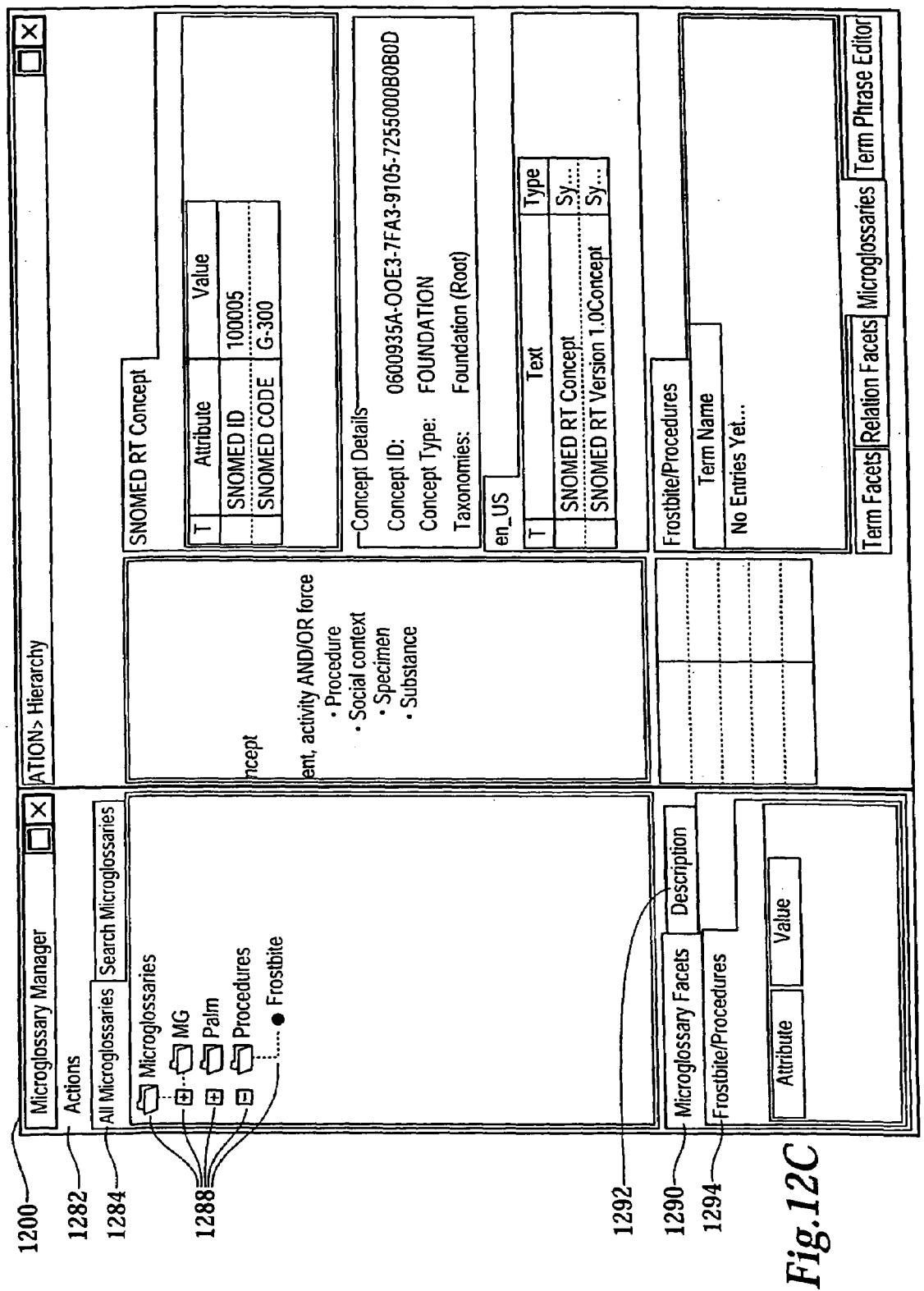
FIG. 12C depicts an illustration of a LExScape graphical user interface display representing a custom list manager in accordance with the present invention.

FIG. 12C depicts an illustration of a LExScape graphical user interface display representing custom list manager 1200 in accordance with the present invention. Menu item 1282 contains selections for all actions that may be performed on custom lists. Custom lists 1288 are displayed when tab 1284 is selected. Tab 1286 displays FIG. 12D. Specific information related to a selected custom list can be viewed by selecting tabs 1290, 1292 and 1294.

To edit a microglossary, the user selects the microglossary and the "Edit Microglossary Properties" option on the "Action" menu of the Microglossary Manager. This results in the display of a dialog box that allows the user to modify the name, group name and description of the microglossary.

To create a microglossary, the user selects "New Microglossary" from the "Action" menu of the Microglossary Manager. A dialog box is then displayed enabling the user to enter a name, group name and description for the new microglossary.

Microglossaries can be opened in a number of ways. First, the user opens the Microglossary Manager as described above. The user can then either double-click the desired microglossary or right-click the desired microglossary to display the context menu containing the "Open Microglossary" option.

A microglossary entry is a row in the microglossary that contains a term or term phrase and may also contain the term's associated concept or term facets as well as microglossary entry facets. Any number of terms can be added to a microglossary any number of times. Terms can be added by dragging them onto the cell that contains the words "no entries yet" or on top of terms already listed. New entries are added to the bottom of the list. A couple of ways to add a concept's display term to a microglossary is by dragging the concept to a microglossary from the workbench or from the concept display, both on the GUI display as shown in FIG. 3, or by selecting "Add to Active Microglossary" from the "Edit" menu of the GUI display as shown in FIG. 3.

Microglossary term phrase entries can be replaced by highlighting and then right-clicking the microglossary entry. The user then selects the "Edit Term Phrase" option from the resultant menu. Other terms and/or phrases can then be used to build the new term phrase. Once the desired term phrase has been created, the user then selects the destination as either the workbench or "Replace in Microglossary." The user can also edit existing phrases in microglossaries by dragging them back to the term phrase editor.

User-defined facets can be associated with either entire microglossaries or with individual entries (rows) within a microglossary. To add facets to an entire microglossary, the user first selects or creates an appropriate facet definition. Then, the user opens the Microglossary Manager as described above. Next, the user highlights the microglossary with which the facet definition is to be associated. A facet panel will become visible at the bottom of the Microglossary Manager. The user then right-clicks the facet panel and selects "Add Facet" from the resultant menu. A dialog box appears with a drop down selection box from which the user can select an available facet. The label for the text data entry box indicates the type of data expected (string, floating point or integer, for example). The user enters the facet value in the data entry box and then clicks "Add."

Microglossary entry facets associate miscellaneous data with individual entries in a microglossary. To add facets to microglossary entries, the user locates or creates an appropriate facet definition. Then, the user opens the Microglossary Manager as described above and opens the microglossary to which the entry facets are to be added. Next, the user right-clicks the "Term Name" column header and selects "dd Entry Facet Column" from the resultant menu. From the displayed dialog box, the user selects the name of the facet definition to be added and then clicks "OK." Once the entry facet column has been created, entry facet values can be entered/edited by typing directly into the cell in the table at the intersection of the entry row and facet column.

Concept and term facets can be displayed using the Microglossary Manager. After opening the desired microglossary, the user right-clicks on the "Term Name" column header and selects either the "Display Concept Facet Column" or the "Display Term Facet Column" from the resultant menu. Select facets for inclusion in the microglossary by turning on their display values. The user then clicks "OK."

To copy a term from an open microglossary the user hightlights, then right-clicks the term in the Microglossary Manager, then selects the "Copy to Open Microglossary" option from the resultant menu.

Individual cells (for entry facet columns), rows and columns can be deleted from microglossaries. To delete a microglossary entry, the user highlights, then right-clicks its "Term Name" cell, the selects "Delete Entry" from the resultant menu. To delete an entry facet, the user highlights, then right-clicks the cell to be deleted, then selects the "Delete [entry facet column name] values" from the resultant menu.

Microglossary entries can be rearranged/reordered. Columns can be reordered by clicking and dragging the column header. Rows can be sorted by value in a given column in either ascending or descending order. Rows can also be rearranged manually by clicking and dragging the entry.

Microglossaries can be copied. To accomplish this, the user highlights the microglossary to be copied and selects "Copy Microglossary" from the "Actions" menu of the Microglossary Manager. To close a microglossary, the user right-clicks the desired microglossary in the Microglossary Manager and selects "Close Microglossary" from the resultant menu. To delete a microglossary, the user right-clicks the desired microglossary in the Microglossary Manager and selects "Delete Microglossary" from the resultant menu.

Microglossaries can be searched for terms or properties (name, group or description) or any combination of these elements. To search a microglossary, the user selects the "Search" tab in the Microglossary Manager. Next, the user selects the search scope, such as properties, terms or both and a type of search, such as exact match, contains or starts with. Then, the user enters a search string into the text box and clicks "Search." Search results can be displayed any number of ways, including in a hierarchical manner similar to the listing of microglossaries in the Microglossaries Manager. Users can use microglossary search results to navigate by either double-clicking the microglossary in the search results or right-clicking the microglossary in the search results and selecting "Open Microglossary" from the resultant menu.

FIG. 12D depicts an illustration of a LExScape graphical user interface display representing a custom list search screen with results in accordance with the present invention. Custom lists can be searched for properties 1272*a*, terms 1272*b* or both 1272*c*. The search type can be exact match 1274*a*, contains 1274*b* or starts with 1274*c*. The search term is entered in box 1276. The search commences when search 1278 is pressed. Search results are listed in box 1280. The custom list 1281 in which the search term appears is emphasized.

Microglossaries can be exported for use in other applications. Microglossaries can be exported individually, as a set or entirely. As described above in relation to exporting concepts, the export file formats currently available are XML, CSV and query set. The export process places each microglossary in a separate file in a directory named after the microglossary group name. The export directory is currently specified in a separate properties file under the section "Export Properties."

To export all microglossaries, the user selects "Export All Microglossaries" from the "Actions" menu of the Microglossaries Manager. The export process for single and multiple microglossaries is similar to that previously described in relation to exporting concepts. To export a single microglossary, the user highlights the desired microglossary, right-clicks and either selects "Export Now" or "Mark for Export." The latter adds the microglossary to an export list. The former invokes the export process. To export numerous microglossaries, the user highlights and marks each microglossary, individually adding them to the export list.

While exporting all or a single microglossary automatically displays the list, marking microglossaries for export requires an extra step. The user must select "Export Now" from the "Actions" menu of the Microglossary Manager. Eventually, each microglossary export procedure displays the list of microglossaries marked for export. At this point, the user can remove microglossaries from the list, include related concepts and/or enable filters as previously described in relation to exporting concepts. After making selections, the user clicks "Next." The procedure then differs based on whether or not filters have been enabled.

If filters have been enabled, a dialog box is displayed allowing the user to define and add filters based on facets. Various types of filters can be used, such as "include-if-present" and "exclude-if-present." Selecting "Next" resumes the basic export procedure.

At this point, the user is allowed to select the format into which the concepts will be exported. If the microglossaries are to be exported in CSV format, additionally selections related to delimination will be required. As with Concept exports in CSV format, the user can select the set of facet values to export as columns in the output. The export may also be sorted by term text or by facet value. After the selections have been made, the user clicks "Next" to continue. The system then displays an export message indicating that the user may complete the export by selecting "Finish," can the export by selecting "Stop Export" and/or save the export criteria, but do not export the microglossaries. The system displays status messages as the export progresses.

FIG. 12E depicts an illustration of a LExScape graphical user interface display representing export formats in accordance with the present invention. Formats such as XML 1253*a*, query set 1253*b* and CSV 1253*c* can be selected. The user can decide to exclude column headers from the export by selecting box 1255. If the user selects CSV 1253*c* as the export format, the list of facet values in box 1259 becomes accessible for the user to select specific facet values to include in the export. Additionally, if the user selects CSV 1253*c* as the export format, the user may either accept the default values or indicate values for field quote string 1257*a*, field separator string 1257*b*, value quote string 1257*c* and value separator string 1257*d*. The values may be empty. The export may be sorted by selecting box 1261 and indicating sort by term text 1263*a* or sort by facet value 1263*b*. If the export is to be sorted by facet value 1263*b*, drop down selection box 1265 becomes accessible for the user to select on which facet type to sort. Back 1267 essentially clears export choices. Cancel 1271 closes the dialog box without exporting. Next 1269 performs the export.

Figure 13A:
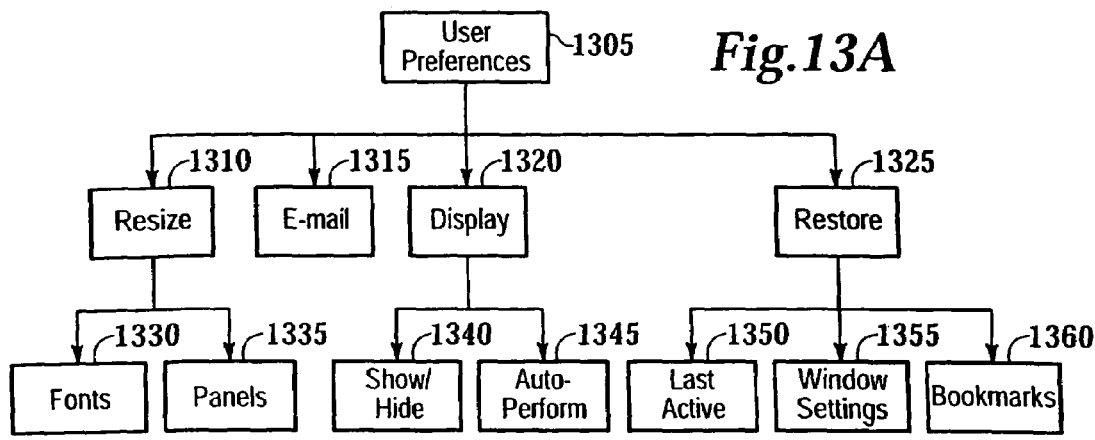
FIG. 13A depicts a flow diagram of personalizing the user environment in accordance with the present invention.

FIG. 13 depicts a flow diagram of personalizing the user environment in accordance with the present invention. The user can modify user preferences in block 1305 by resizing in block 1310, setting e-mail parameters in block 1315, setting display parameters in block 1320 and setting restore parameters in block 1325. The user can resize fonts in block 1330 and panels in block 1335. Display parameters in block 1320 include show/hide settings in block 1340 and auto-perform parameters in block 1345. Finally, the user can restore last active settings in block 1350, window settings in block 1355 and bookmarks in block 1360.

Several of the elements of FIG. 3 can be resized and some user preferences can be set. For instance, the font size for concept display 305 of FIG. 3 can be modified. Located around focus concept 330 will be a circle. By clicking and dragging the circle, the user can resize the font. To shrink fonts in concept display 305, the user selects the circle and moves the mouse toward the center of the circle. To expand fonts in concept display 305, the user selects the circle and moves the mouse toward the edges of the GUI display. To resize the panels, the user places the mouse cursor over either a vertical or horizontal bar separating the panels. When the cursor turns into a double-sided arrow, the user then clicks and drags the bar to resize the panel.

There are several things that can be accomplished by setting user preferences: the user's preferred configurations can be saved for later use; e-mail information can be recorded to facilitate sending system error messages; facets to be included in the content display can be identified; and the type of value to be included in the attributes panel can be selected for relations. To access user preferences, the user selects "Edit Preferences" from the "Edit" menu of the GUI display as shown in FIG. 3.

The user can modify a wide variety of preferences, such as: restore last active concept; restore window position and dimensions; restore concept bookmarks; enable plex resizing. The last active concept is the concept that was in focus when the user last exited the system. If preferred, the system can restore that concept rather than returning the user to the root concept. Restoring window positions and dimensions restores the window settings established in previous sessions. Restoring concept bookmarks saves bookmarks. Enabling plex resizing turns on the circle in the concept display, enabling the user to resize display fonts. The user may also enter an e-mail address and SMTP host and set facet and relation display properties.

The user can also set navigation and modeling settings, such as: view coding concepts in navigation hierarchy, view retired concepts in navigation hierarchy; auto-replace subsumed parents on addParent; and restore term candidates. Viewing coding concepts in navigation hierarchy includes coding concepts in the concept display. View retired concepts in navigation hierarchy includes retired concepts in the concept display. Auto-replace subsumed parents on addparent, in effect, performs a delete parent on a child's current location, followed by an add new child to the new location when a user attempts to add a child that is already a descendent of the concept WITHOUT asking the user to verify the modification. Restore term candidates restores term candidates in the workbench from the previous session.

Figure 13B:
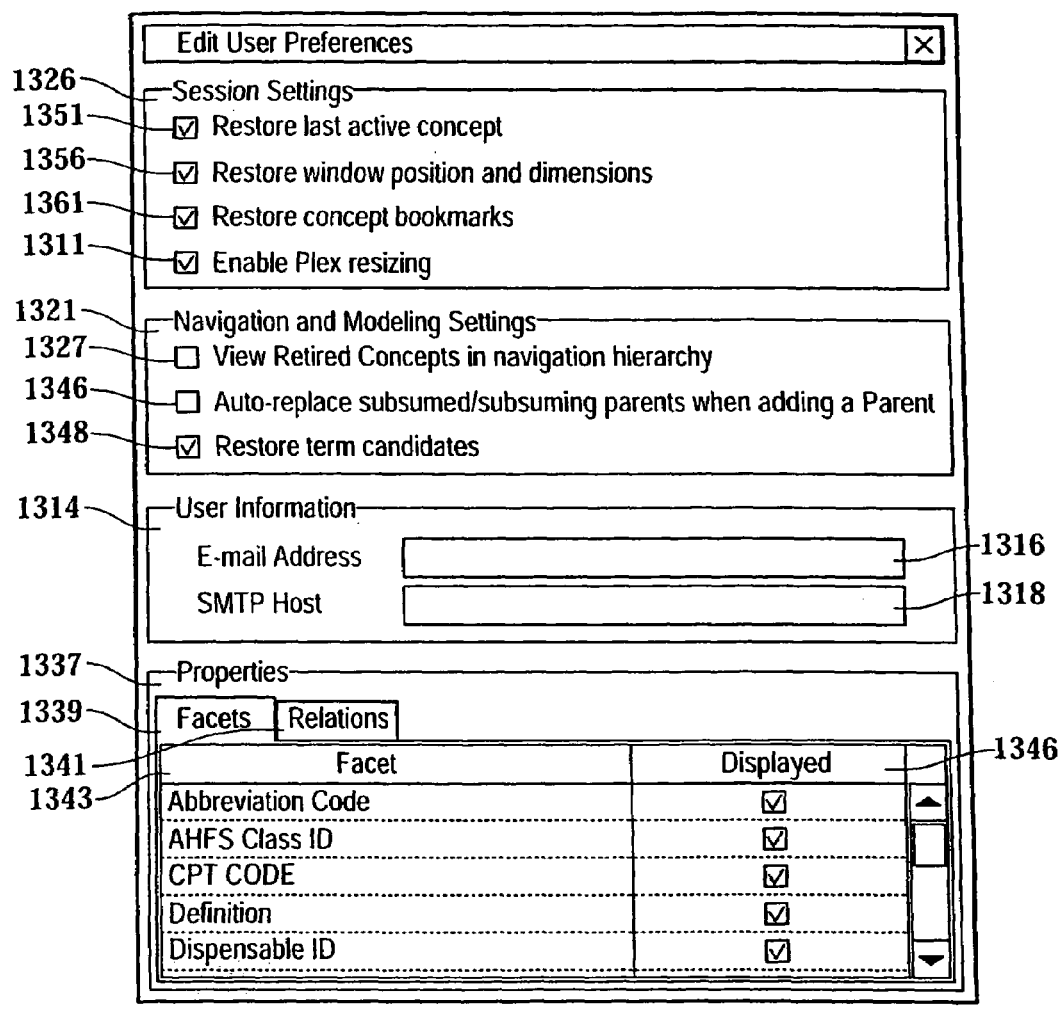
FIG. 13B depicts an illustration of a LExScape graphical user interface display representing user preferences in accordance with the present invention.

FIG. 13B depicts an illustration of a LExScape graphical user interface display representing user preferences in accordance with the present invention. Box 1326 contains session settings, such as restore last active concept 1351, restore window position and dimensions 1356, restore concept bookmarks 1361 and enable plex resizing 1311. Box 1321 contains navigation and modeling settings, such as view retired concepts in navigation hierarchy 1327, auto-replace subsumed/subsuming parents when adding a parent 1346 and restore term candidates 1348. Box 1314 contains user information, such as e-mail address 1316 and SMTP host 1318. Box 1337 contains show/hide properties for such objects as facets 1339 and relations 1343. Column 1341 displays the object name. Column 1346 enables the user to select or deselect the display option.

Figure 14:
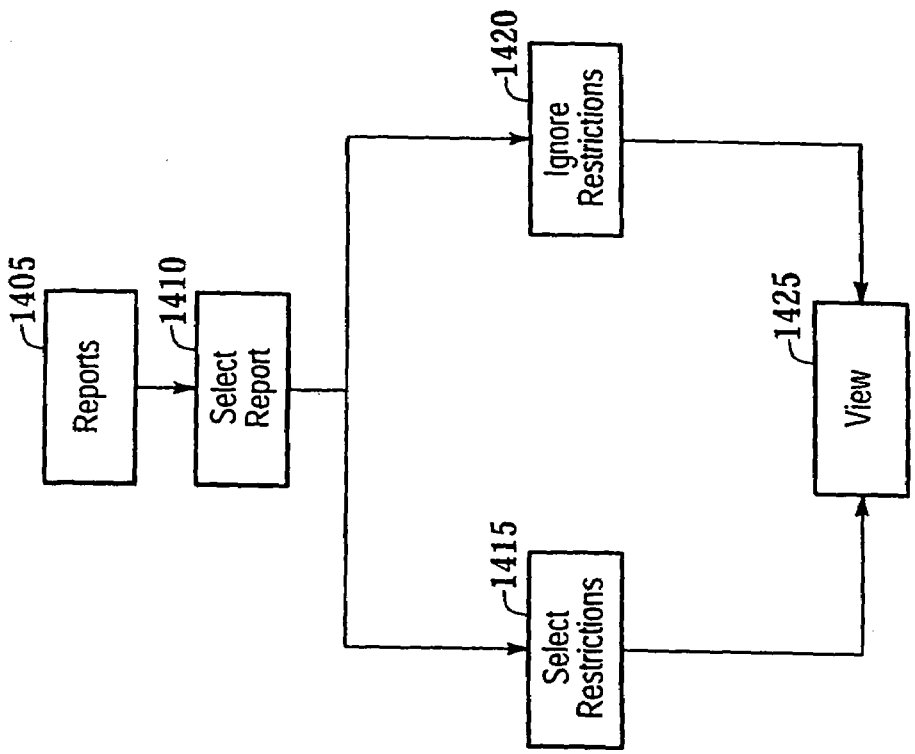
FIG. 14 depicts a flow diagram of reporting in accordance with the present invention.

FIG. 14 depicts a flow diagram of reporting in accordance with the present invention. The user commences report generation in block 1405. The report is selected in block 1410. Report restrictions are selected in block 1415 or ignored in block 1420. The report is then viewed in block 1425.

There are currently a limited number of predefined reports included in the present invention. They can be accessed from the "Reports" menu item of the GUI display as shown in FIG. 3. These predefined reports are: duplicate terms, concepts with duplicate facet values, and branch factor. Duplicate terms creates a list of terms associated with concepts of the same type that have the same display term. After selecting this report, the user can select one or more concept types and apply those types as report restrictions. The user can also choose to "Ignore Restriction." Concepts with duplicate facet values creates a list of concepts that share a facet with identical values. Branch factor reports concepts with greater than a user-specified number of children.

Figure 15:
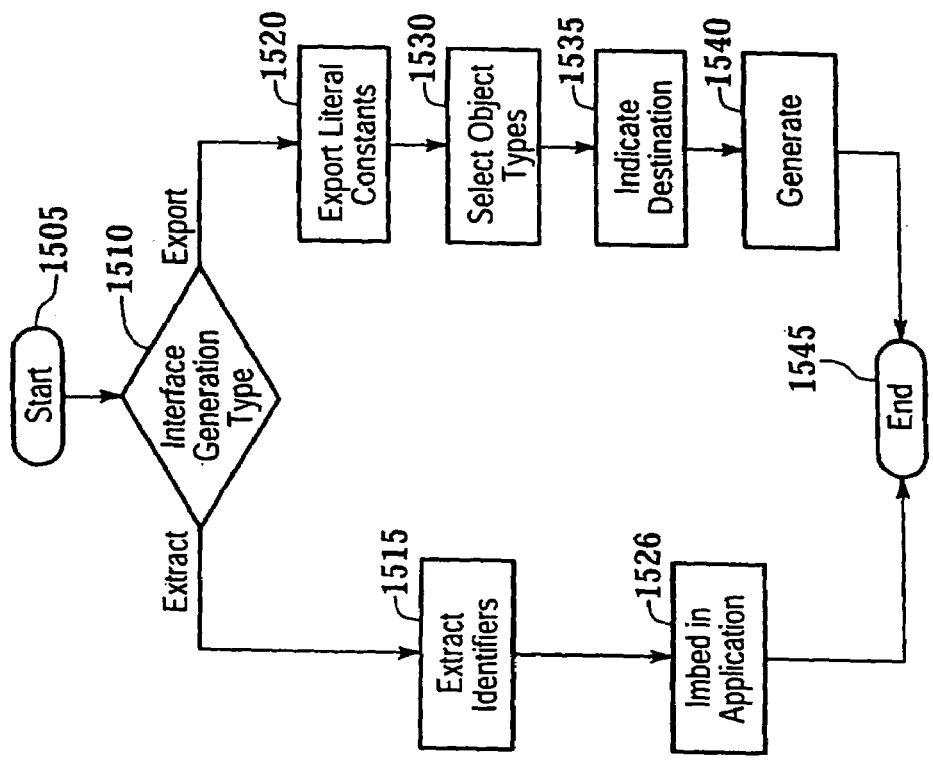
FIG. 15 depicts a flow diagram of generating interfaces in accordance with the present invention.

FIG. 15 depicts a flow diagram of generating interfaces in accordance with the present invention. The interface generation starts in terminal 1505. The user then decides the type of interface generation in decision point 1510. If the user chooses to extract identifiers in block 1515, the user can then imbed (hard-code) the identifiers in to the interface application. Alternatively, the user can choose to have the present invention export literal constants in block 1520. The user selects object types in block 1530, indicates the storage destination in block 1535 and sets the system interface generation process into motion in block 1540. The interface generation process ends in terminal 1545.

Java interface files can be generated using the present invention. There are currently two (2) main ways to accomplish this. The first is to extract the unique identifiers from the present invention and imbed them directly in the application. The second is to use the present invention to export literal constants of the unique identifiers as Java interface files.

When the present invention creates Java interface files by exporting literal constants of unique identifiers, it includes only identifiers for relation definitions, facet definitions, concept types and taxonomies. The generated interface files can then be included in an application so that these objects can be referenced by their nicknames, rather than by hard-coding the unique identifiers.

To generate interface code using the present invention, the user would select "Generate Interface Code" from the "File" menu of the GUI display as shown in FIG. 3. A dialog box is then displayed containing available object types, such as concept type, relation definition, facet definition and taxonomy. All are currently selected by default. The user can individually select and/or deselect object types. The user then indicates the destination for the interface code either by accepting the given location, typing in the location or browsing the system to select the location. The user then clicks "Generate" to generate code.

Now referring to FIG. 16, an illustration of a LExIndex 112 graphical user interface display in accordance with the present invention is shown. The end user determines the set of concepts used in the indexing operation by creating a custom query set. A query set is a subset of the concepts in the Lexicon chosen for relevance to the indexing task to be performed. All of the Terms 124 associated with each Concept 122 form the "evidence phrases" to determine when a concept is referenced in a given document. Using the Lexicon content to construct query sets, the LExIndex tools provide a powerful mechanism to tag documents with relevant Concepts 122. Concept-based indexing is a powerful model for organizing documents around the Lexicon Concept(s) that are referred to in the document.

While specific alternatives to steps of the present invention have been described herein, additional alternatives not specifically disclosed but known in the art are intended to fall within the scope of this invention. Thus, it is understood that other applications of the present invention will be apparent to those skilled in the art upon the reading of the described embodiments and a consideration of the appended claims and drawings.

What is claimed is:

1. A system for interfacing with a multi-level data structure comprising:
   a computer;
   a display communicably connected to the computer;
   a memory communicably connected to the computer for storing the multi-level data structure;
   a computer program resident on the computer for:
      selecting a health language concept object stored in the multi-level data structure;
      displaying a first image in a first window comprising an alphanumeric string representing the selected health language concept object on the display;
      displaying one or more second images on the display and along one or more respective geometrical rays originating from a central region of the first image, each second image comprising an alphanumeric string representing a parent health language concept object of the selected health language concept object and displaying a first symbol on the display along each respective geometrical ray originating from the central region of the first image;
      if the selected health language concept object has one or more child health language concept objects, displaying one or more third images on the display and along one or more respective geometrical rays originating from the central region of the first image, each third image comprising an alphanumeric string representing a child health language concept object of the selected health language concept object and displaying a second symbol on the display along each respective geometrical ray originating from the central region of the first image;

if the selected health language concept object has one or more lateral health language concept objects, displaying one or more fourth images on the display and along one or more respective geometrical rays originating from a central region of the first image, each fourth image comprising an alphanumeric string representing a lateral health language concept object of the selected health language concept object and displaying a third symbol on the display along each respective geometrical ray originating from the central region of the first image;

positioning all second, third, and fourth images in locations around the first image such that the first image comprises a geometrical center in the first window relative to all symbols on the display;

displaying an editable text list in a second window in response to objects selected in the first window, the text list comprising information relating to at least one of a selected health language concept object, parent health language concept object, child health language concept object, and a lateral health language concept object; and displaying one or more attributes of the selected health language concept object in a first viewing area on the display, wherein the attributes comprise at least one of a billing code and a medical code;

receiving input for one of modifying, removing, and creating relationships between health language concept objects.

2. The system as recited in claim 1 wherein the computer program:

selects a new health language concept object from one of the selected health language concept object, the one or more parent health language concept objects, one or more children health language concept objects, and one or more lateral health language concept objects;

displays a fifth image on the display comprising the selected new health language concept object; displays one or more sixth images on the display, each sixth image comprising a parent health language concept object of the selected new health language concept object;

displays a fourth symbol on the display illustrating an association between each sixth image and the fifth image;

if the selected new health language concept object has one or more child health language concept objects, displays one or more seventh images on the display, each seventh image comprising a child health language concept object of the selected new health language concept object, and displays a fifth symbol on the display illustrating an association between each seventh image and the fifth image; and if the selected health language new concept object has one or more lateral health language concept objects, displays one or more eighth image comprising a lateral health language concept object of the selected new health language concept object, and displays a sixth symbol on the display illustrating an association between each eighth image and the fifth image.

3. The system as recited in claim 1 wherein the first, second, third and fourth images comprise text strings and wherein the first image is highlighted.

4. The system as recited in claim 1 wherein the computer program displays the first, second, third and fourth images, and the first, second and third symbols within a second viewing area on the display.

5. The system as recited in claim 4 wherein the computer program displays one or more terms associated with the selected health language concept object in a third viewing area on the display.

6. The system as recited in claim 5 wherein the computer program displays a work area for temporarily storing terms in a fourth viewing area on the display.

7. The system as recited in claim 1 wherein the computer program:

selects either a microglossary panel, a term facet panel, a relations facet panel or a term phrase editor panel; and displays the selected panel in a second viewing area on the display.

* * * * *